United States Patent
Thompson Smith et al.

(10) Patent No.: US 12,128,199 B2
(45) Date of Patent: Oct. 29, 2024

(54) HYBRID TRANSSEPTAL DILATOR AND METHODS OF USING THE SAME

(71) Applicant: Boston Scientific Medical Device Limited, Galway (IE)

(72) Inventors: Melanie Thompson Smith, Toronto (CA); Gareth Davies, Toronto (CA); Linus Hoi Che Leung, Toronto (CA)

(73) Assignee: Boston Scientific Medical Device Limited, Galway (IE)

( * ) Notice: Subject to any disclaimer, the term of this patent is extended or adjusted under 35 U.S.C. 154(b) by 0 days.

(21) Appl. No.: 17/813,945

(22) Filed: Jul. 21, 2022

(65) Prior Publication Data
US 2022/0355087 A1  Nov. 10, 2022

Related U.S. Application Data

(63) Continuation of application No. 16/068,589, filed as application No. PCT/IB2017/050065 on Jan. 6, 2017, now Pat. No. 11,426,565.
(Continued)

(51) Int. Cl.
*A61M 29/00* (2006.01)
*A61B 17/34* (2006.01)
(Continued)

(52) U.S. Cl.
CPC ......... *A61M 29/00* (2013.01); *A61B 17/3415* (2013.01); *A61B 17/3478* (2013.01);
(Continued)

(58) Field of Classification Search
CPC .. A61M 29/00; A61M 2205/32; A61M 25/09; A61M 2205/582; A61M 2055/582;
(Continued)

(56) References Cited

U.S. PATENT DOCUMENTS

| 175,254 A | 3/1876 | Oberly |
|---|---|---|
| 827,626 A | 7/1906 | Gillet |

(Continued)

FOREIGN PATENT DOCUMENTS

| JP | 2006-334242 A | 12/2006 |
|---|---|---|
| JP | 2015-533091 A | 11/2015 |

(Continued)

OTHER PUBLICATIONS

International Search Report and Written Opinion received for PCT Patent Application No. PCT/IB2017/050065, mailed on Apr. 18, 2017, 16 pages.

(Continued)

*Primary Examiner* — Tan-Uyen T Ho
*Assistant Examiner* — Bridget E. Rabaglia
(74) *Attorney, Agent, or Firm* — Nelson Mullins Riley & Scarborough LLP

(57) ABSTRACT

An apparatus is disclosed for an optimized transseptal procedure that reduces the number of devices that are used in order to minimize procedural time, complexity and cost. The apparatus comprises a hybrid dilator that comprises the combined functionality of a transseptal sheath and dilator assembly. The hybrid dilator comprises: a dilator shaft defining a lumen for receiving a crossing device therethrough, a distal tip having an outer diameter which tapers down to an outer diameter of the crossing device for providing a smooth transition and a hub coupled with a side arm coupled to the dilator shaft.

20 Claims, 16 Drawing Sheets

Related U.S. Application Data

(60) Provisional application No. 62/275,907, filed on Jan. 7, 2016.

(51) Int. Cl.
*A61B 18/14* (2006.01)
*A61M 25/06* (2006.01)
*A61M 25/09* (2006.01)
*A61B 17/00* (2006.01)
*A61B 17/22* (2006.01)
*A61B 18/00* (2006.01)
*A61B 90/00* (2016.01)

(52) U.S. Cl.
CPC ......... *A61B 18/1477* (2013.01); *A61M 25/06* (2013.01); *A61M 25/09* (2013.01); *A61B 2017/00247* (2013.01); *A61B 2017/22038* (2013.01); *A61B 2017/22042* (2013.01); *A61B 2017/22047* (2013.01); *A61B 2018/00351* (2013.01); *A61B 2018/1425* (2013.01); *A61B 2090/033* (2016.02); *A61B 2090/062* (2016.02); *A61B 2090/0807* (2016.02); *A61M 2205/32* (2013.01); *A61M 2205/582* (2013.01)

(58) Field of Classification Search
CPC ............ A61M 29/02; A61M 2029/025; A61M 25/0662; A61M 2025/0681; A61M 25/0023; A61M 25/01; A61M 25/00; A61B 17/3415; A61B 17/3478
See application file for complete search history.

(56) References Cited

U.S. PATENT DOCUMENTS

| | | |
|---|---|---|
| 848,711 A | 4/1907 | Weaver |
| 1,072,954 A | 9/1913 | Junn |
| 1,279,654 A | 9/1918 | Charlesworth |
| 1,918,094 A | 7/1933 | Geekas |
| 1,996,986 A | 4/1935 | Weinberg |
| 2,021,989 A | 11/1935 | De Master |
| 2,146,636 A | 2/1939 | Lipchow |
| 3,429,574 A | 2/1969 | Williams |
| 3,448,739 A | 6/1969 | Stark et al. |
| 3,575,415 A | 4/1971 | Fulp et al. |
| 3,595,239 A | 7/1971 | Petersen |
| 4,129,129 A | 12/1978 | Amrine |
| 4,244,362 A | 1/1981 | Anderson |
| 4,401,124 A | 8/1983 | Guess et al. |
| 4,639,252 A | 1/1987 | Kelly et al. |
| 4,641,649 A | 2/1987 | Walinsky et al. |
| 4,669,467 A | 6/1987 | Willett et al. |
| 4,682,596 A | 7/1987 | Bales et al. |
| 4,790,311 A | 12/1988 | Ruiz |
| 4,790,809 A | 12/1988 | Kuntz |
| 4,793,350 A | 12/1988 | Mar et al. |
| 4,807,620 A | 2/1989 | Strul et al. |
| 4,832,048 A | 5/1989 | Cohen |
| 4,840,622 A | 6/1989 | Hardy |
| 4,863,441 A | 9/1989 | Lindsay et al. |
| 4,884,567 A | 12/1989 | Elliott et al. |
| 4,892,104 A | 1/1990 | Ito et al. |
| 4,896,671 A | 1/1990 | Cunningham et al. |
| 4,928,693 A | 5/1990 | Goodin et al. |
| 4,936,281 A | 6/1990 | Stasz |
| 4,960,410 A | 10/1990 | Pinchuk |
| 4,977,897 A | 12/1990 | Hurwitz |
| 4,998,933 A | 3/1991 | Eggers et al. |
| 5,006,119 A | 4/1991 | Acker et al. |
| 5,019,076 A | 5/1991 | Yamanashi et al. |
| 5,047,026 A | 9/1991 | Rydell |
| 5,081,997 A | 1/1992 | Bosley et al. |
| 5,098,431 A | 3/1992 | Rydell |
| 5,112,048 A | 5/1992 | Kienle |
| 5,154,724 A | 10/1992 | Andrews |
| 5,201,756 A | 4/1993 | Horzewski et al. |
| 5,209,741 A | 5/1993 | Spaeth |
| 5,211,183 A | 5/1993 | Wilson |
| 5,221,256 A | 6/1993 | Mahurkar |
| 5,230,349 A | 7/1993 | Edwin |
| 5,281,216 A | 1/1994 | Klicek |
| 5,300,068 A | 4/1994 | Rosar et al. |
| 5,300,069 A | 4/1994 | Hunsberger et al. |
| 5,314,418 A | 5/1994 | Takano et al. |
| 5,318,525 A | 6/1994 | West et al. |
| 5,327,905 A | 7/1994 | Avitall |
| 5,364,393 A | 11/1994 | Auth et al. |
| 5,372,596 A | 12/1994 | Klicek et al. |
| 5,380,304 A | 1/1995 | Parker |
| 5,397,304 A | 3/1995 | Truckai |
| 5,403,338 A | 4/1995 | Milo |
| 5,423,809 A | 6/1995 | Klicek |
| 5,425,382 A | 6/1995 | Golden et al. |
| 5,490,859 A | 2/1996 | Mische et al. |
| 5,497,774 A | 3/1996 | Swartz et al. |
| 5,507,751 A | 4/1996 | Goode et al. |
| 5,509,411 A | 4/1996 | Littmann et al. |
| 5,540,681 A | 7/1996 | Strul et al. |
| 5,545,200 A | 8/1996 | West et al. |
| 5,555,618 A | 9/1996 | Winkler |
| 5,571,088 A | 11/1996 | Lennox et al. |
| 5,575,766 A | 11/1996 | Swartz et al. |
| 5,575,772 A | 11/1996 | Lennox |
| 5,599,347 A | 2/1997 | Hart et al. |
| 5,605,162 A | 2/1997 | Mirzaee et al. |
| 5,617,878 A | 4/1997 | Taheri |
| 5,622,169 A | 4/1997 | Golden et al. |
| 5,624,430 A | 4/1997 | Eton et al. |
| 5,667,488 A | 9/1997 | Lundquist et al. |
| 5,673,695 A | 10/1997 | McGee et al. |
| 5,674,208 A | 10/1997 | Berg et al. |
| 5,683,366 A | 11/1997 | Eggers et al. |
| 5,720,744 A | 2/1998 | Eggleston et al. |
| 5,741,249 A | 4/1998 | Moss et al. |
| 5,766,135 A | 6/1998 | Terwilliger |
| 5,779,688 A | 7/1998 | Imran et al. |
| 5,810,764 A | 9/1998 | Eggers et al. |
| 5,814,028 A | 9/1998 | Swartz et al. |
| 5,830,214 A | 11/1998 | Flom et al. |
| 5,836,875 A | 11/1998 | Webster, Jr. |
| 5,849,011 A | 12/1998 | Jones et al. |
| 5,851,210 A | 12/1998 | Torossian |
| 5,885,227 A | 3/1999 | Finlayson |
| 5,888,201 A | 3/1999 | Stinson et al. |
| 5,893,848 A | 4/1999 | Negus et al. |
| 5,893,885 A | 4/1999 | Webster, Jr. |
| 5,904,679 A | 5/1999 | Clayman |
| 5,916,210 A | 6/1999 | Winston |
| 5,921,957 A | 7/1999 | Killion et al. |
| 5,931,818 A | 8/1999 | Werp et al. |
| 5,944,023 A | 8/1999 | Johnson et al. |
| 5,951,482 A | 9/1999 | Winston et al. |
| 5,957,842 A | 9/1999 | Littmann et al. |
| 5,964,757 A | 10/1999 | Ponzi |
| 5,967,976 A | 10/1999 | Larsen et al. |
| 5,989,276 A | 11/1999 | Houser et al. |
| 6,007,555 A | 12/1999 | Devine |
| 6,009,877 A | 1/2000 | Edwards |
| 6,013,072 A | 1/2000 | Winston et al. |
| 6,017,340 A | 1/2000 | Cassidy et al. |
| 6,018,676 A | 1/2000 | Davis et al. |
| 6,030,380 A | 2/2000 | Auth et al. |
| 6,032,674 A | 3/2000 | Eggers et al. |
| 6,048,349 A | 4/2000 | Winston et al. |
| 6,053,870 A | 4/2000 | Fulton, III |
| 6,053,904 A | 4/2000 | Scribner et al. |
| 6,056,747 A | 5/2000 | Saadat et al. |
| 6,063,093 A | 5/2000 | Winston et al. |
| 6,093,185 A | 7/2000 | Ellis et al. |
| 6,106,515 A | 8/2000 | Winston et al. |
| 6,106,520 A | 8/2000 | Laufer et al. |
| 6,117,131 A | 9/2000 | Taylor |
| 6,120,494 A | 9/2000 | Jonkman |

(56) References Cited

U.S. PATENT DOCUMENTS

| | | |
|---|---|---|
| 6,142,992 A | 11/2000 | Cheng et al. |
| 6,146,380 A | 11/2000 | Racz et al. |
| 6,155,264 A | 12/2000 | Ressemann et al. |
| 6,156,031 A | 12/2000 | Aita et al. |
| 6,171,305 B1 | 1/2001 | Sherman |
| 6,179,824 B1 | 1/2001 | Eggers et al. |
| 6,193,676 B1 | 2/2001 | Winston et al. |
| 6,193,715 B1 | 2/2001 | Wrublewski et al. |
| 6,210,408 B1 | 4/2001 | Chandrasekaran et al. |
| 6,217,575 B1 | 4/2001 | Devore et al. |
| 6,221,061 B1 | 4/2001 | Engelson et al. |
| 6,228,076 B1 | 5/2001 | Winston et al. |
| 6,245,054 B1 | 6/2001 | Fuimaono et al. |
| 6,267,758 B1 | 7/2001 | Daw et al. |
| 6,283,983 B1 | 9/2001 | Makower et al. |
| 6,292,678 B1 | 9/2001 | Hall et al. |
| 6,293,945 B1 | 9/2001 | Parins et al. |
| 6,296,615 B1 | 10/2001 | Brockway et al. |
| 6,296,636 B1 | 10/2001 | Cheng et al. |
| 6,302,898 B1 | 10/2001 | Edwards et al. |
| 6,304,769 B1 | 10/2001 | Arenson et al. |
| 6,315,777 B1 | 11/2001 | Comben |
| 6,328,699 B1 | 12/2001 | Eigler et al. |
| 6,360,128 B2 | 3/2002 | Kordis et al. |
| 6,364,877 B1 | 4/2002 | Goble et al. |
| 6,385,472 B1 | 5/2002 | Hall et al. |
| 6,394,976 B1 | 5/2002 | Winston et al. |
| 6,395,002 B1 | 5/2002 | Ellman et al. |
| 6,419,674 B1 | 7/2002 | Bowser et al. |
| 6,428,551 B1 | 8/2002 | Hall et al. |
| 6,450,989 B2 | 9/2002 | Pubrul et al. |
| 6,475,214 B1 | 11/2002 | Moaddeb |
| 6,485,485 B1 | 11/2002 | Winston et al. |
| 6,508,754 B1 | 1/2003 | Liprie et al. |
| 6,524,303 B1 | 2/2003 | Garibaldi |
| 6,530,923 B1 | 3/2003 | Dubrul et al. |
| 6,554,827 B2 | 4/2003 | Chandrasekaran et al. |
| 6,562,031 B2 | 5/2003 | Chandrasekaran et al. |
| 6,562,049 B1 | 5/2003 | Norlander et al. |
| 6,565,562 B1 | 5/2003 | Shah et al. |
| 6,607,529 B1 | 8/2003 | Jones et al. |
| 6,632,222 B1 | 10/2003 | Edwards et al. |
| 6,639,999 B1 | 10/2003 | Cookingham et al. |
| 6,650,923 B1 | 11/2003 | Lesh et al. |
| 6,651,672 B2 | 11/2003 | Roth |
| 6,662,034 B2 | 12/2003 | Segner et al. |
| 6,663,621 B1 | 12/2003 | Winston et al. |
| 6,702,811 B2 | 3/2004 | Stewart et al. |
| 6,709,444 B1 | 3/2004 | Makower |
| 6,723,052 B2 | 4/2004 | Mills |
| 6,733,511 B2 | 5/2004 | Hall et al. |
| 6,740,103 B2 | 5/2004 | Hall et al. |
| 6,752,800 B1 | 6/2004 | Winston et al. |
| 6,755,816 B2 | 6/2004 | Ritter et al. |
| 6,811,544 B2 | 11/2004 | Schaer |
| 6,814,733 B2 | 11/2004 | Schwartz et al. |
| 6,820,614 B2 | 11/2004 | Bonutti |
| 6,834,201 B2 | 12/2004 | Gillies et al. |
| 6,842,639 B1 | 1/2005 | Winston et al. |
| 6,852,109 B2 | 2/2005 | Winston et al. |
| 6,855,143 B2 | 2/2005 | Davison et al. |
| 6,860,856 B2 | 3/2005 | Ward et al. |
| 6,869,431 B2 | 3/2005 | Maguire et al. |
| 6,911,026 B1 | 6/2005 | Hall et al. |
| 6,951,554 B2 | 10/2005 | Johansen et al. |
| 6,951,555 B1 | 10/2005 | Suresh et al. |
| 6,955,675 B2 | 10/2005 | Jain |
| 6,970,732 B2 | 11/2005 | Winston et al. |
| 6,980,843 B2 | 12/2005 | Eng et al. |
| 7,029,470 B2 | 4/2006 | Francischelli et al. |
| 7,056,294 B2 | 6/2006 | Khairkhahan et al. |
| 7,083,566 B2 | 8/2006 | Tornes et al. |
| 7,112,197 B2 | 9/2006 | Hartley et al. |
| 7,335,197 B2 | 2/2008 | Sage et al. |
| 7,618,430 B2 | 11/2009 | Scheib |
| 7,651,492 B2 | 1/2010 | Wham |
| 7,666,203 B2 | 2/2010 | Chanduszko et al. |
| 7,678,081 B2 | 3/2010 | Whiting et al. |
| 7,682,360 B2 | 3/2010 | Guerra |
| 7,828,796 B2 | 11/2010 | Wong et al. |
| 7,900,928 B2 | 3/2011 | Held et al. |
| 8,114,110 B2 | 2/2012 | Bednarek et al. |
| 8,192,425 B2 | 6/2012 | Mirza et al. |
| 8,257,323 B2 | 9/2012 | Joseph et al. |
| 8,388,549 B2 | 3/2013 | Paul et al. |
| 8,500,697 B2 | 8/2013 | Kurth et al. |
| 8,911,415 B2 | 12/2014 | Knapp |
| 11,339,579 B1 | 5/2022 | Stearns |
| 11,426,565 B2 * | 8/2022 | Thomspon Smith . A61M 29/00 |
| 2001/0012934 A1 | 8/2001 | Chandrasekaran et al. |
| 2001/0021867 A1 | 9/2001 | Kordis et al. |
| 2002/0019644 A1 | 2/2002 | Hastings et al. |
| 2002/0022781 A1 | 2/2002 | McLntire et al. |
| 2002/0022836 A1 | 2/2002 | Goble et al. |
| 2002/0035361 A1 | 3/2002 | Houser et al. |
| 2002/0087153 A1 | 7/2002 | Roschak et al. |
| 2002/0087156 A1 | 7/2002 | Maguire et al. |
| 2002/0111618 A1 | 8/2002 | Stewart et al. |
| 2002/0123749 A1 | 9/2002 | Jain |
| 2002/0147485 A1 | 10/2002 | Mamo et al. |
| 2002/0169377 A1 | 11/2002 | Khairkhahan et al. |
| 2002/0188302 A1 | 12/2002 | Berg et al. |
| 2002/0198521 A1 | 12/2002 | Maguire |
| 2003/0032929 A1 | 2/2003 | McGuckin |
| 2003/0040742 A1 | 2/2003 | Underwood et al. |
| 2003/0083560 A1 * | 5/2003 | Osypka .................. A61N 1/056 600/374 |
| 2003/0144658 A1 | 7/2003 | Schwartz et al. |
| 2003/0158480 A1 | 8/2003 | Tornes et al. |
| 2003/0163153 A1 | 8/2003 | Scheib |
| 2003/0225392 A1 | 12/2003 | McMichael et al. |
| 2004/0015162 A1 | 1/2004 | McGaffigan |
| 2004/0024396 A1 | 2/2004 | Eggers |
| 2004/0030328 A1 | 2/2004 | Eggers et al. |
| 2004/0044350 A1 | 3/2004 | Martin et al. |
| 2004/0073243 A1 | 4/2004 | Sepetka et al. |
| 2004/0077948 A1 | 4/2004 | Molante et al. |
| 2004/0097881 A1 | 5/2004 | Brustad et al. |
| 2004/0116851 A1 | 6/2004 | Johansen et al. |
| 2004/0127963 A1 | 7/2004 | Uchida et al. |
| 2004/0133113 A1 | 7/2004 | Krishnan |
| 2004/0133130 A1 | 7/2004 | Ferry et al. |
| 2004/0143256 A1 | 7/2004 | Bednarek |
| 2004/0147950 A1 | 7/2004 | Mueller et al. |
| 2004/0181213 A1 | 9/2004 | Gondo |
| 2004/0230188 A1 | 11/2004 | Cioanta et al. |
| 2005/0004585 A1 | 1/2005 | Hall et al. |
| 2005/0010208 A1 | 1/2005 | Winston et al. |
| 2005/0049628 A1 | 3/2005 | Schweikert et al. |
| 2005/0059966 A1 | 3/2005 | McClurken et al. |
| 2005/0065507 A1 | 3/2005 | Hartley et al. |
| 2005/0070949 A1 | 3/2005 | Bakos et al. |
| 2005/0085806 A1 | 4/2005 | Auge et al. |
| 2005/0096529 A1 | 5/2005 | Cooper et al. |
| 2005/0101984 A1 | 5/2005 | Chanduszko et al. |
| 2005/0119556 A1 | 6/2005 | Gillies et al. |
| 2005/0137527 A1 | 6/2005 | Kunin |
| 2005/0149012 A1 | 7/2005 | Penny et al. |
| 2005/0203504 A1 | 9/2005 | Wham et al. |
| 2005/0203507 A1 | 9/2005 | Truckai et al. |
| 2005/0228364 A1 * | 10/2005 | Braga ................ A61B 17/3415 606/1 |
| 2005/0261607 A1 | 11/2005 | Johansen et al. |
| 2005/0288631 A1 | 12/2005 | Lewis et al. |
| 2006/0041253 A1 | 2/2006 | Newton et al. |
| 2006/0064062 A1 | 3/2006 | Gurusamy et al. |
| 2006/0074398 A1 | 4/2006 | Whiting et al. |
| 2006/0079769 A1 | 4/2006 | Whiting et al. |
| 2006/0079787 A1 | 4/2006 | Whiting et al. |
| 2006/0079884 A1 | 4/2006 | Manzo et al. |
| 2006/0085054 A1 | 4/2006 | Zikorus et al. |
| 2006/0089638 A1 | 4/2006 | Carmel et al. |
| 2006/0106375 A1 | 5/2006 | Werneth et al. |
| 2006/0135962 A1 | 6/2006 | Kick et al. |

(56) References Cited

U.S. PATENT DOCUMENTS

| | | |
|---|---|---|
| 2006/0142756 A1 | 6/2006 | Davies et al. |
| 2006/0189972 A1 | 8/2006 | Grossman |
| 2006/0241586 A1 | 10/2006 | Wilk |
| 2006/0247672 A1 | 11/2006 | Vidlund et al. |
| 2006/0264927 A1 | 11/2006 | Ryan |
| 2006/0276710 A1 | 12/2006 | Krishnan |
| 2007/0060879 A1 | 3/2007 | Weitzner et al. |
| 2007/0066975 A1 | 3/2007 | Wong et al. |
| 2007/0118099 A1 | 5/2007 | Trout, III |
| 2007/0123964 A1 | 5/2007 | Davies et al. |
| 2007/0167775 A1 | 7/2007 | Kochavi et al. |
| 2007/0185522 A1* | 8/2007 | Davies .................. A61M 29/00 606/191 |
| 2007/0208256 A1 | 9/2007 | Marilla |
| 2007/0225681 A1 | 9/2007 | House |
| 2007/0270791 A1 | 11/2007 | Wang et al. |
| 2008/0039865 A1 | 2/2008 | Shaher et al. |
| 2008/0042360 A1 | 2/2008 | Veikley |
| 2008/0086120 A1 | 4/2008 | Mirza et al. |
| 2008/0097213 A1 | 4/2008 | Carlson et al. |
| 2008/0108987 A1 | 5/2008 | Bruszewski et al. |
| 2008/0146918 A1 | 6/2008 | Magnin et al. |
| 2008/0171934 A1 | 7/2008 | Greenan et al. |
| 2008/0208121 A1 | 8/2008 | Youssef et al. |
| 2008/0275439 A1 | 11/2008 | Francischelli et al. |
| 2009/0105742 A1 | 4/2009 | Kurth et al. |
| 2009/0125097 A1 | 5/2009 | Bruszewski et al. |
| 2009/0138009 A1 | 5/2009 | Viswanathan et al. |
| 2009/0163850 A1 | 6/2009 | Betts et al. |
| 2009/0171276 A1* | 7/2009 | Bednarek ............ A61B 17/3478 604/170.01 |
| 2009/0177114 A1 | 7/2009 | Chin et al. |
| 2009/0264977 A1 | 10/2009 | Bruszewski et al. |
| 2010/0087789 A1 | 4/2010 | Leeflang et al. |
| 2010/0094258 A1* | 4/2010 | Shimogami ......... A61M 25/005 606/191 |
| 2010/0125282 A1 | 5/2010 | Machek et al. |
| 2010/0168684 A1 | 7/2010 | Ryan |
| 2010/0179632 A1 | 7/2010 | Bruszewski et al. |
| 2010/0191142 A1 | 7/2010 | Paul et al. |
| 2010/0194047 A1 | 8/2010 | Sauerwine |
| 2010/0249491 A1* | 9/2010 | Farnan .............. A61M 25/0068 600/16 |
| 2011/0046619 A1 | 2/2011 | Ducharme |
| 2011/0152716 A1 | 6/2011 | Chudzik et al. |
| 2011/0160592 A1 | 6/2011 | Mitchell |
| 2011/0190763 A1 | 8/2011 | Urban et al. |
| 2012/0232546 A1 | 9/2012 | Mirza et al. |
| 2012/0265055 A1 | 10/2012 | Melsheimer et al. |
| 2012/0330156 A1 | 12/2012 | Brown et al. |
| 2013/0150793 A1* | 6/2013 | Beissel ................. A61M 29/00 604/171 |
| 2013/0178841 A1 | 7/2013 | Reid, Jr. |
| 2013/0184551 A1 | 7/2013 | Paganelli et al. |
| 2013/0184735 A1 | 7/2013 | Fischell et al. |
| 2013/0282084 A1 | 10/2013 | Mathur et al. |
| 2014/0025036 A1 | 1/2014 | Bierman et al. |
| 2014/0094645 A1 | 4/2014 | Lafontaine et al. |
| 2014/0200396 A1 | 7/2014 | Lashinski et al. |
| 2014/0206987 A1 | 7/2014 | Urbanski et al. |
| 2014/0276432 A1* | 9/2014 | Bierman ........... A61M 25/0097 604/167.03 |
| 2014/0296769 A1 | 10/2014 | Hyde et al. |
| 2015/0173782 A1 | 6/2015 | Garrison et al. |
| 2015/0173794 A1 | 6/2015 | Kurth et al. |
| 2015/0351793 A1 | 12/2015 | Bierman et al. |
| 2016/0220741 A1 | 8/2016 | Garrison et al. |
| 2019/0021763 A1 | 1/2019 | Zhou et al. |
| 2019/0247035 A1 | 8/2019 | Gittard et al. |

FOREIGN PATENT DOCUMENTS

| | | |
|---|---|---|
| WO | 2015/048795 A2 | 4/2015 |
| WO | 2015/136338 A1 | 9/2015 |
| WO | 2015/192109 A1 | 12/2015 |

OTHER PUBLICATIONS

Patent Corporation Treaty, International Preliminary Report on Patentability, dated Jul. 10, 2018.

* cited by examiner

SECTION A-A

SECTION B-B

HYBRID TRANSSEPTAL DILATOR AND METHODS OF USING THE SAME

CROSS REFERENCE TO RELATED APPLICATIONS

The present application is a continuation of U.S. patent application Ser. No. 16/068,589, filed on 12 Dec. 2018, which is a national phase application of International Application No. PCT/IB2017/050065, filed on 6 Jan. 2017, which claims priority from U.S. Provisional Application Ser. No. 62/275,907, filed on 7 Jan. 2016, each of which are incorporated in their entireties.

TECHNICAL FIELD

The present disclosure relates to a medical device for using in accessing the cardiovascular system. More particularly the present disclosure relates to a hybrid transseptal dilator for facilitating a transseptal procedure for providing left heart access

BRIEF DESCRIPTION OF THE DRAWINGS

In order that the invention may be readily understood, embodiments of the invention are illustrated by way of examples in the accompanying drawings, in which.

DETAILED DESCRIPTION

Figure 1A:
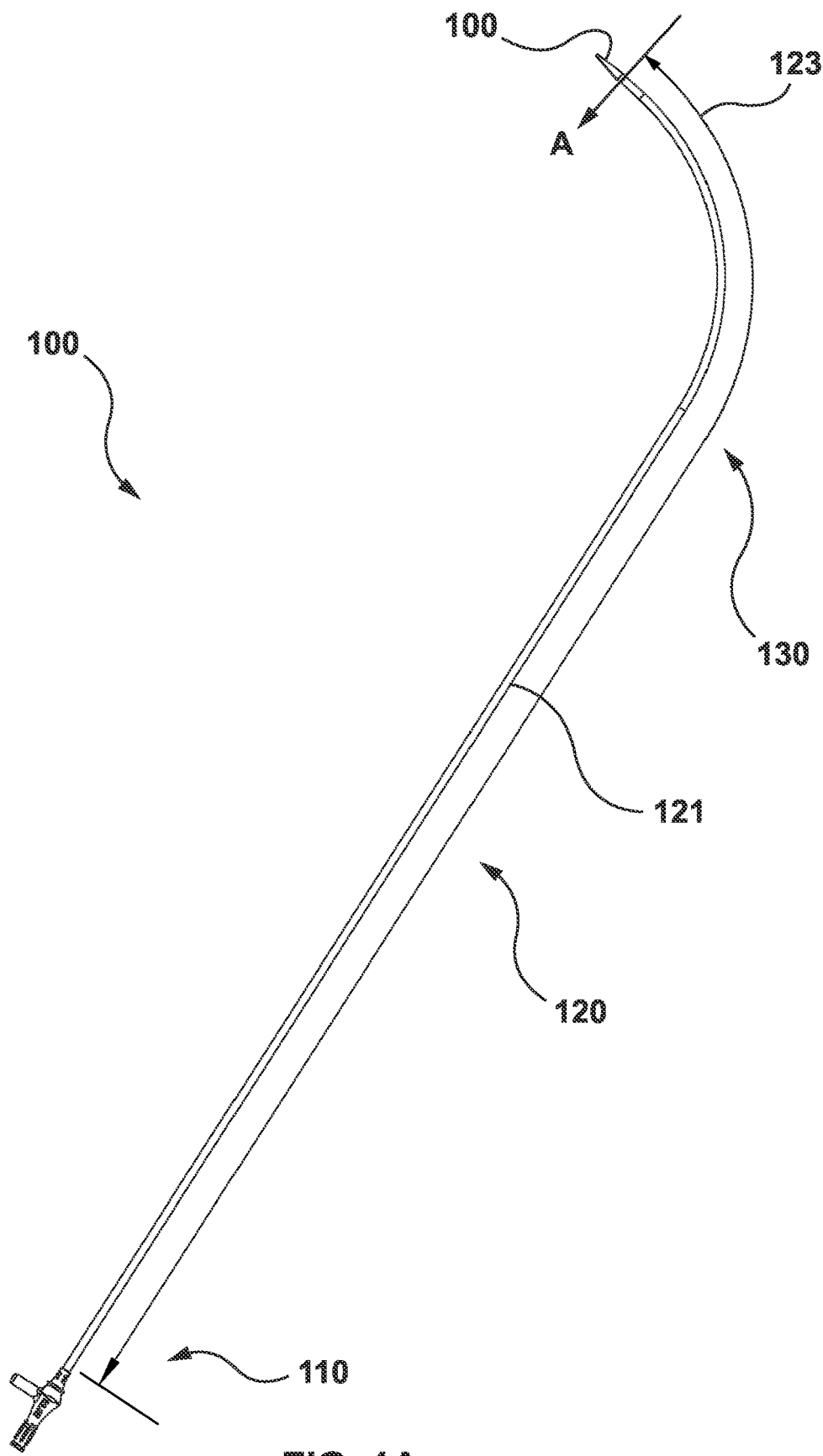
FIG. 1A is an illustration of a hybrid dilator, in accordance with an embodiment of the present invention.

When performing a transseptal procedure to gain access to the left atrium of a heart, a physician typically uses a sheath and dilator to support a crossing or puncturing device. In some cases, a physician may not be able to cross through to the left atrium sheath as the transition between sheath and dilator may get stuck or snag at the tissue boundary, and as a result the sheath may not be able to cross through the perforation (or it crosses with difficulty). In other words, the tissue may get hung up at the sheath/dilator interface. Thus, the use of multiple device in a transseptal procedure may make it difficult for the operator to complete the procedure due to the material transitions between various devices which may get caught at the septal tissue interface. The problem of a transseptal puncture being performed using a crossing device which is supported by a sheath and dilator set having a transition which may snag on tissue when crossing the septum, can be addressed by using a hybrid dilator (described herein) instead of the sheath and dilator set to thereby eliminate the transition, wherein the hybrid dilator has the appropriate functionality (flexibility, pushability, torqueability, distal taper, etc.) to facilitate a smooth crossing.

In one broad aspect, embodiments of the present invention include a hybrid dilator for use with a crossing device in tissue puncturing procedures, the hybrid dilator comprising: a dilator shaft defining a lumen for receiving a crossing device therethrough, the dilator shaft being structured to provide support for the crossing device when the crossing device is used to create a puncture in a tissue; and a distal tip having an outer diameter which tapers down to an outer diameter of the crossing device for providing a smooth transition between the crossing device and the distal tip when the crossing device is inserted through the lumen and protrudes beyond the distal tip. In some such embodiments, the dilator shaft comprises an inner layer, an outer layer, and a torque layer therebetween.

In another broad aspect, embodiments of the present invention include a kit for puncturing a tissue, the kit comprising: a crossing device having a puncturing feature; and a hybrid dilator, wherein the dilator has a dilator shaft defining a lumen for receiving the crossing device therethrough, the dilator shaft being structured to provide support for the crossing device when the crossing device is used to create a puncture in a tissue. The hybrid dilator also includes a distal tip which has an outer diameter which substantially tapers down to an outer diameter of the crossing device for cooperatively providing a smooth profile when the hybrid dilator is advanced through a tissue over the crossing device. In some embodiments of the kit, the crossing device is a mechanical needle with a sharp tip, while in some other embodiments, the crossing device is configured for delivering energy to a tissue.

In another broad aspect, embodiments of the present invention include a system for puncturing a tissue, the system comprising: a crossing device having a puncturing feature which is operable to deliver energy to a tissue; an electrosurgical generator which is operable to provide energy to the puncturing feature; and a hybrid dilator, wherein the hybrid dilator has a dilator shaft defining a lumen for receiving the crossing device therethrough, the dilator shaft being structured to provide support for the crossing device when the crossing device is used to create a puncture in a tissue. The hybrid dilator also includes a distal tip having an outer diameter which substantially tapers down to an outer diameter of the crossing device for cooperatively providing a smooth profile when the hybrid dilator is advanced through a tissue over the crossing device.

In yet another broad aspect, embodiments of the present invention comprise a method of using a hybrid dilator and a crossing device for puncturing a septum of a heart, the method comprising the steps of: (a) positioning a distal tip of the hybrid dilator at a desired site of the septum; (b) using the hybrid dilator for supporting a crossing device, located within a lumen of the hybrid dilator, as the crossing device is advanced beyond the distal tip of the hybrid dilator to puncture the septum; and (c) advancing the hybrid dilator over the crossing device thereby dilating the desired site.

In one broad aspect, a hybrid dilator is provided as a composite device that comprises one or more requisite features of a transseptal dilator or sheath or a combination thereof in a single device, in order to provide the combined functionality of a transseptal sheath and dilator assembly in an optimized manner. Some of these features that provide the combined functionality of a sheath and dilator assembly may include shaft rigidity, curvature and internal and exterior tapers that may be incorporated along a distal portion of the hybrid dilator including along a distal tip to facilitate crossing of the hybrid dilator. Additionally, in some case the hybrid dilator may include features that facilitate handling of the hybrid dilator and/or provide directionality information such as tactile cues or indications to convey the direction of the distal tip curvature for facilitating the transseptal procedure. In some instances these features may be incorporated into a proximal portion of the hybrid dilator such as within a combined proximal hub.

In another broad aspect, an optimized method is provided to perform a transseptal medical procedure. The method provides for streamlining the procedural workflow by providing a hybrid dilator that includes enhanced functionalities of a conventional transseptal sheath and dilator assembly. With the hybrid dilator of the present invention, a reduced number of devices may be required in order to complete the transseptal procedure, which enhances procedural efficiency while reducing procedural time and complexity.

In some situations, where a standard sheath and dilator assembly are successful in completing an initial transseptal access procedure, the sheath may not be large enough to support subsequent advancement of a relatively larger outer diameter (OD) catheter for treatment to the left side of the heart. As a result, the sheath and dilator assembly may have to be removed and the catheter may then be advanced over a guidewire that is in place across the septum to thereby be advanced into the left side of the heart. In other instances, the physician may want to use a large delivery sheath for complex procedures (such as \left atrial appendage closure/occlusion procedures) and knows that it may not be possible to cross with that product, so they may introduce a standard transseptal kit (that includes a sheath, dilator and guidewire) in order to cross and pre-dilate the septum. The three piece kit may then be removed for exchange, and then discarded, which results in the three products (sheath, dilator, guidewire) only being used for a short procedural time period. Thus, in some cases, the sheath and dilator assembly may only be useful to perform an initial transseptal puncture, leading to waste due to multiple devices being used. Furthermore, performing a transseptal procedure using multiple devices contributes to an increase in procedural time and complexity, and additional cost. Furthermore, with the emergence of more left atrial clinical interventions, there is a growing need for safe and reliable transseptal solutions.

In some embodiments, an oversized hybrid dilator is provided that reduces the number of physical/geometric transitions as well as the number of material transitions which can both cause difficulties or tactile obstructions for physicians when completing transseptal or other tissue crossings. Some examples include smooth lines and tapers to facilitate a seamless transition across tissue.

Additionally, the present inventors have discovered a method to perform a transseptal medical procedure that streamlines the procedural workflow by providing a hybrid dilator that replaces a conventional transseptal sheath and dilator assembly. With the hybrid dilator of the present invention a reduced number of devices may be required in order to complete a transseptal procedure. This reduces the number of parts that a physician is required to prepare and assemble for the transseptal procedure and introduce into the patient. The present method provides a dilator that is usable with a guidewire for access that replaces a sheath, dilator, and guidewire assembly.

With specific reference now to the drawings in detail, it is stressed that the particulars shown are by way of example and for purposes of illustrative discussion of certain embodiments of the present invention only. Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

In some embodiments, a single piece/unitary device in the form of a hybrid dilator is provided that provides smooth tapers functions to facilitate both the crossing and the exchange of devices in a trans-septal procedure while still providing the physician with tactile feedback and distal curve indication that are substantially equivalent to those provided by a sheath/dilator assembly.

Figure 1B:
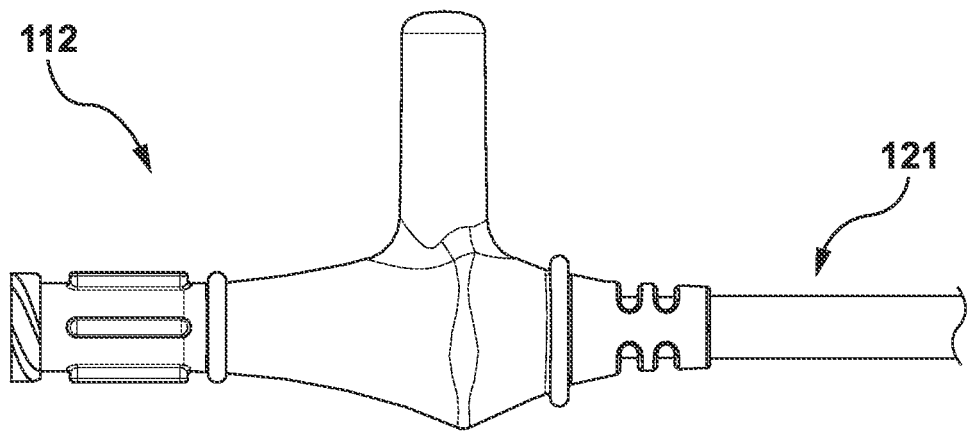
FIG. 1B is an illustration of a proximal portion of the hybrid dilator of FIG. 1A.
Figure 1C:
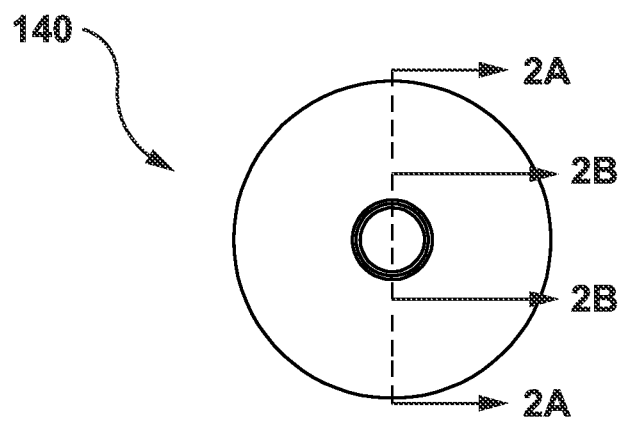
FIG. 1C is a front end view of a distal tip of the hybrid dilator of FIG. 1A.
Figure 1D:
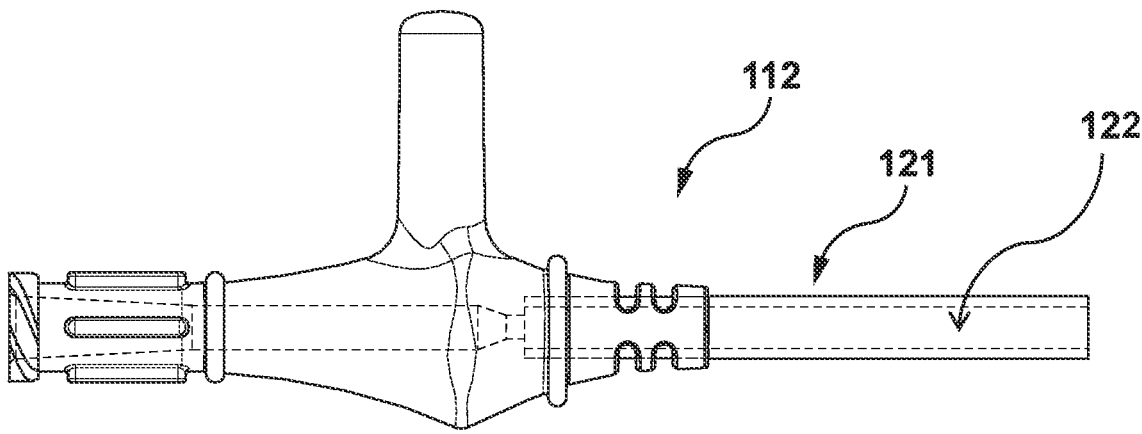
FIG. 1D is an illustration of a proximal portion of the hybrid dilator of FIG. 1A.

In accordance with an embodiment of the present invention, a hybrid dilator 100 is provided, as shown in FIG. 1A. The hybrid dilator 100 comprises a combination of features that provide a dual functionality of a sheath and a dilator for facilitating a transseptal puncture procedure while avoiding disadvantages of conventional sheath and dilator assemblies. The hybrid dilator 100 provides the smoothness of a standard transseptal dilator with the control of a standard transseptal sheath. More specifically, the hybrid dilator 100 functions as a single device that removes the need for using a conventional sheath/dilator assembly and eliminates the need for assembly, resulting in less waste. The hybrid dilator 100 comprises a sheath-like handle with familiar torque and tactile control. In the specific example shown, the hybrid dilator 100 defines a proximal portion 110 comprising a molded combination proximal hub 112, as shown in FIGS. 1B and 1D. A distal portion 120 is coupled to the proximal portion 110 comprising a dilator shaft. The dilator shaft extends from the proximal end and defines a curved distal end 130 that terminates in a distal tip 140, as additionally shown in FIG. 1C.

Dilator Shaft/Support and Columnar Strength/Positioning

The dilator shaft is formed from a smooth distal tubing 121 that is coupled to the molded proximal hub 112. The distal tubing 121 defines a lumen 122 there-through that narrows at the distal tip 140 and which may be used to flush the device prior to use. In some embodiments, since the hybrid dilator 100 is provided a single unitary device, this means that one product is to be flushed unlike the prior art sheath/dilator assembly where each product requires flushing. The dilator shaft provides mechanical properties to best facilitate procedural activities. At the distal tip 140, as illustrated further in FIG. 2A, the distal tubing 121 transitions through a smooth external taper T3 that widens in the proximal direction to a greater outer diameter OD than a conventional transseptal kit dilator so as to dilate the septum to an appropriate size for the subsequent delivery device or equipment that may be used. The OD of the distal tubing 121 is substantially constant from the proximal edge of distal tip 140 till the proximal hub 112 where the distal tubing is coupled or attached thereto. In some such embodiments, the OD of the hybrid dilator 100 may vary based on the application and clinical use. In some embodiments, the size of hybrid dilator 100 is from about 12 French to about 20 French. In a specific example, the hybrid dilator has a size of about 12.5 French (outer diameter of about 0.163 inches (0.414 cm) to about 0.166 inches (0.421 cm)). In another example, the hybrid dilator has a size of about 15 French (outer diameter of about 0.193 inches (0.490 cm) to about 0.205 inches (0.521 cm)).

Distal End Curvature

In some embodiments of the present invention, the distal end 130 of the hybrid dilator 100 may be curved as shown in FIG. 1A. Alternatively, the distal end 130 of the hybrid dilator may be straight. In some embodiments where the distal end 130 of the hybrid dilator 100 is curved, the hybrid dilator 100, in combination with a puncturing device such as a needle, forms a trajectory that is substantially equivalent to the trajectory achieved by the combination of a sheath/dilator/needle assembly of a conventional transseptal kit to provide physicians with a predictable and repeatable path for completing a transseptal puncture. The curved distal end 130 facilitates advancement of the hybrid dilator 100 in conjunction with the puncturing device to initiate a transseptal puncture.

In some such embodiments, the hybrid dilator 100 comprises a shaft formed from distal tubing 121 that is sufficiently rigid to enable positioning of a crossing device such as a puncturing needle or a guidewire to be advanced through it while maintaining the position of the assembly at a desired site, such as a fossa of a septum. As such, the hybrid dilator 100 functions to provide support and columnar strength to facilitate placement of the crossing device at the desired location. As disclosed above and as shown in FIG. 1A, distal tubing 121 tapers proximally from the distal tip 140 to a greater OD defining a dilating interface to allow dilation of the puncture site 510 (FIG. 6A) to facilitate additional devices to be advanced there-through.

Distal Tip

Figure 2A:
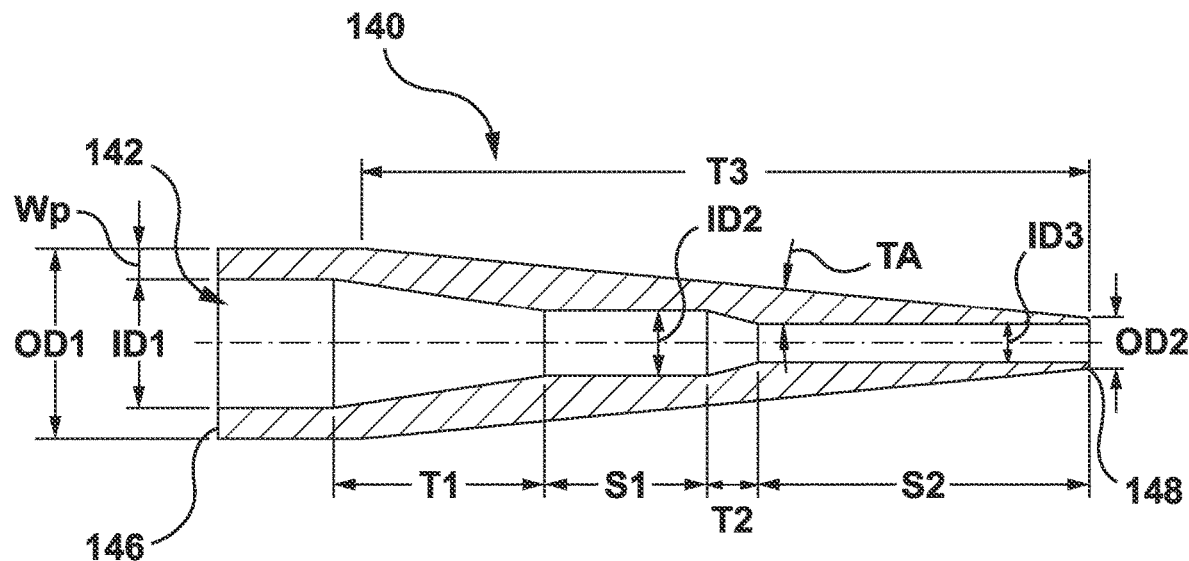
FIG. 2A. is a cross-sectional view of the distal tip of a hybrid dilator taken along the lines 2A-2A of FIG. 1C.

More specifically, as shown in FIG. 2A, the distal tip 140 provides a lumen 142 that is appropriate for a crossing device such as a puncturing device to be inserted therethrough and defines a relatively thin wall to facilitate controlled puncture. In some such examples, the puncturing device is a mechanical needle or an RF puncturing device that is usable with the hybrid dilator 100. The hybrid dilator 100 provides a restricted distal internal diameter (as shown by ID2 and ID3) at the distal tip 140 to control the distance by which the puncture device with a transseptal needle (with a narrow distal portion) protrudes from the hybrid dilator 100. The narrowest distal portion of a compatible puncturing device has an outer diameter less than ID3 whereby it extends into and through length S2 of lumen 142, and beyond distal edge 148, while, typically, a part of the puncturing device having an outer diameter greater than ID3 and less than ID2 will be seated in internal taper T2. Consequently, the dimension of length S2 is significant in determining the distance the puncturing device protrudes from the hybrid dilator 1. In some such embodiments, this allows the hybrid dilator 100 to meet the same standard as existing transseptal dilators in that it controls the distance by which a transseptal needle can protrude when fully inserted therein. Additionally, as described previously, the distal tip 140 provides an external taper T3 that allows the dilator OD to transition from a narrow OD2 at a distal most end or distal edge 148 of the distal tip 140, to a wider OD1 at its proximal edge 146. In some such examples, the hybrid dilator 100 has smooth lines and a smooth external taper T3 to facilitate a seamless transition across tissue. In some such examples, the hybrid dilator 100 functions to reduce the number of physical or geometric transitions or material transitions which can cause difficulties and/or create tactile obstructions hindering a physician's ability to complete a transseptal or other tissue crossing.

In typical examples, as shown in FIGS. 1A and 2A, the dilator shaft includes a distal tubing 121 which, in some examples, comprises a high density polyethylene (HDPE) Tubing. In some such embodiments, the HDPE has a hardness from about 55 shore D to about 70 shore D, and in a specific example, the HDPE hardness is about 67 shore D. In typical embodiments, the distal tubing 121 comprises material that meets the functional requirements of a transseptal sheath/dilator kit. In some such examples, the distal tubing 121 comprises a straight shaft that transitions into curved distal end 130. The distal tip 140 comprises a tapered tip with a smooth external taper T3, having a taper angle TA of about 5.5°+/−1° degrees, and internal geometry which provides a controlled internal diameter (ID) to provide a predicable needle extension length. In some embodiments, the length of the external taper T3 ranges from about 0.4 inches (1 cm) to about 1 inch (2.5 cm). In some such examples, the taper length for external taper T3 is equal to about 0.646" or about 1.6 cm. The distal tubing 121 has an inner diameter ID1 that is equal to about 0.109" (0.277 cm) and an outer diameter OD1 that is equal to about 0.166" (0.422 cm) along its proximal portion (or proximal length 123), which extends from the proximal hub 112 to adjacent the distal tip 140, as shown in FIG. 1A. In the example shown in FIG. 2A, the inner diameter at the distal tip 140 tapers down along internal taper T1 from ID1 to a relatively smaller inner diameter ID2. In one such embodiment, the taper length for internal taper T1 is equal to about 0.22" (cm 0.56) and ID2 extends for a distance S1 for about 0.100" (0.254 cm) and ID2 has a value equal to about 0.056" (0.142 cm). In some examples, the inner diameter then further transitions from ID2 along an internal taper T2 to an even smaller inner diameter ID3. In some embodiments, the distal portion of the distal tip (length S2) has a length from about 0.71 cm to about 0.74 cm, and in some more specific embodiments, a length from about 0.721 cm to about 0.726 cm. In a specific instance, taper T2 extends for a distance equal to about 0.044" (0.112 cm), where the ID3 is equal to about 0.034" (0.086 cm) and extends for a length S2 of about 0.285" (0.724 cm). In some alternative embodiments, S1 is equal to zero, whereby internal taper T1 and internal taper T2 are adjacent to each other to thereby provide a smooth transition of internal diameter. Some alternative embodiments include the dilator shaft substantially comprising a low density polyethylene or a polyether ether ketone, with some such embodiments of the dilator shaft having a hardness from about 40 shore D to about 85 shore D.

Some embodiments of the dilator shaft comprised of a relatively harder material (e.g. HDPE) have an inner diameter ID1 of about 0.072 inches (0.18 cm) to about 0.11 inches (0.28 cm). Other embodiments of the dilator shaft comprised of a relatively softer material (e.g. polyurethanes, polyether block amide) have an inner diameter ID1 of about 0.050 inches (0.13 cm) to about 0.11 inches (0.28 cm). Polyether block amide (PEBA) is a thermoplastic elastomer (TPE) and is known under the tradenames of VESTAMID® E (Evonik Industries) and Pebax (Arkema).

Figure 2B:
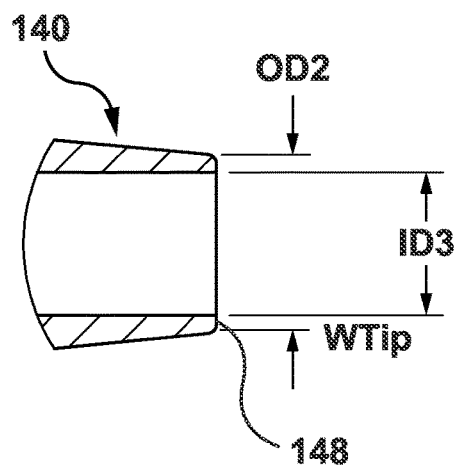
FIG. 2B. is a cross-sectional view of the distal most end of a hybrid dilator taken along the lines 2B-2B of FIG. 1C.

In the example shown in FIG. 2A, having several internal transitions, such as internal taper T1 and internal taper T2, ensures that the hybrid dilator has an OD along its proximal length (OD1) that enables the hybrid dilator 100 to dilate a tissue puncture site to a desired extent, while at the same time allowing the wall thickness $W_p$ of the distal tubing 121 to be maintained to provide shaft rigidity and stiffness that is comparable to a conventional sheath/dilator assembly. The internal geometry of distal tip 140, including dual tapers T1 and T2 and the inner diameter along the distal tip 140, provides for insertion of a puncturing device such as needle there-through and for the desired extension of a needle tip. The internal geometry also helps ensure that the wall thickness $W_{Tip}$ (FIG. 2B) at the distal edge 148 of the distal tip 140 is sufficiently thin to ensure crossing and trackability through the transseptal puncture site. Still furthermore, the dual tapers T1 and T2 ensure that a smooth transition is provided between the relatively wider inner diameter ID1 along the proximal portion of distal tubing 121, and the relatively narrower inner diameter ID3 at the distal edge 148. In some embodiments, the inner diameter ID3 at distal edge 148 is about 0.033 inches (0.084 cm) to about 0.037 inches (0.094 cm) and the outer diameter at distal edge 148 is about 0.040 inches (0.10 cm) to about 0.055 inches (0.14 cm). In one specific example, the inner diameter ID3 at the distal edge 148 is equal to about 0.034" (0.086 cm) (FIG. 2B) and the outer diameter OD2 at the distal edge is equal to about 0.042" (0.107 cm).

In some embodiments, the taper angle TA may range from about 5° to about 15°. In some examples, the taper length of external taper T3 may range from about 1.0 cm to about 1.6 cm. In some embodiments, length of the external taper T3 ranges from about 0.4 inches (1 cm) to about 1 inch (2.5 cm). In one example, the taper length of external taper T3 may be about 1.0 cm with a taper angle TA of about 15°. In some embodiments, the wall thickness WTip at the distal edge 148 of the distal tip 140 is between about 4 thousandths of an inch (0.010 cm) to about 5 thousandths of an inch (0.013 cm). The wall thickness $W_{Tip}$ is sufficient for maintaining mechanical integrity of the distal tip 140 while ensuring that it is not too thick to make it difficult for the distal tip 140 to cross a puncture site within the tissue.

Figure 2C:
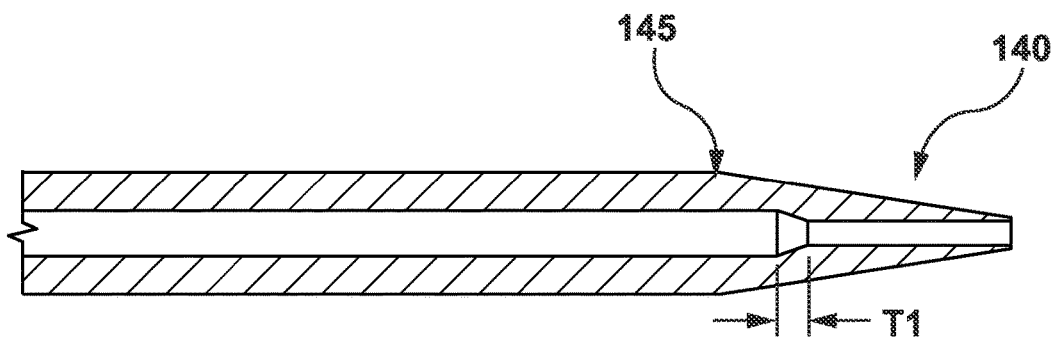
FIG. 2C is an illustration of a distal tip, in accordance with an alternative embodiment of the present invention.

In an alternative embodiment of the present invention, as shown in FIG. 2C, a distal tip 140 may be provided with a single internal taper T1 as shown. As shown, the distal tubing 121 is shown with inner lumen visible.

Wall Thickness, Bending Stiffness and Torque

As discussed earlier with respect to FIG. 2A, the hybrid dilator 100 is an HDPE Dilator with a 12.5 French OD with an 8.5 French ID. The ID and OD are representative of the dimensions along the proximal length 123 of the distal tubing 121. Additionally, the wall thickness Wp along the proximal length 123 is about 25.5 thousandths of an inch (0.065 cm) to about 27.5 thousandths of an inch (0.070 cm). Bending stiffness for the illustrated example is about 3 N/mm and the torque is about 4.5 N cm.

In an alternative embodiment the hybrid dilator is a 12.5 French OD dilator with an 8.5 French ID. The wall thickness Wp along the proximal length 123 of the distal tubing 121 is about 32 thousandths of an inch (0.081 cm). Bending stiffness for the particular example is about 4 N/mm and the torque is about 5 N cm.

In still a further alternative, the hybrid dilator 100 is a 12.5 French OD dilator with a 4.5 French ID. The wall thickness Wp along the proximal length 123 of the distal tubing 121 is about 55 thousandths of an inch (0.140 cm). Bending stiffness for the particular example is about 5.5 N/mm and the torque is about 7 N cm. In another example, the hybrid dilator is a 15 French dilator where the wall thickness is less than about 26.5 thousandths of an inch (0.067 cm) to provide adequate stiffness.

In some embodiments, a HDPE hybrid dilator 100 has: a 12.5F OD which is about 0.162-0.166" (0.411-0.422 cm); a 4.5-8.5F ID (about 0.056-0.115 inches or about 0.142-0.292 cm); a wall thickness from about 0.025" to about 0.055" (about 0.064-0.140 cm), a stiffness of about 3.5 to 5.5 N/mm, and a torque transmission from about 4 to about 7 N cm.

In an alternative embodiment, the dilator shaft is comprised substantially of HDPE and includes: a 12.5 French OD (about 0.162"-0.166" or about 0.411-0.422 cm); an 8.5 French ID (about 0.108"-0.115" or about 0.274-0.2921 cm); a wall thickness from about 23.5 thousandths of an inch (0.06 cm) to about 29 thousandths of an inch (0.074 cm). Such embodiments may have a bending stiffness from about 2.5 to 3.5 N/mm and a torque transmission from about 4 to 4.5 N cm.

In another alternative embodiment, the dilator shaft is HDPE and has: a 12.5 French OD (about 0.162"-0.166" or about 0.411-0.422 cm); a 7.5 French ID (about 0.095"-0.102" or about 0.241-0.259 cm); and a wall thickness which is about 0.03-0.036" (about 0.076-0.091 cm). Bending stiffness for such examples is about 3.5 to 4.5 N/mm and the torque transmission is about 4.5 to 5.5 N cm. In some specific embodiments, the wall thickness is about 32 thousandths of an inch (0.081 cm).

Another alternative embodiment includes the dilator shaft being comprised of HDPE and the shaft having: a 12.5 French OD (about 0.162"-0.166" or about 0.411-0.422 cm); a 4.5 French ID (about 0.056"-0.063" or about 0.142-0.160 cm); and a wall thickness of about 0.05-0.055" (0.127-0.140 cm). Typically, bending stiffness for such embodiments is from about 5 to 6 N/mm and the torque is about 6 N cm to 7 N cm. In some specific embodiments, the wall thickness is about 55 thousandths of an inch (0.140 cm).

In some embodiments of the present invention Torque may range from about 1.0 N cm to about 7 N cm over a length of about 50 cm. In some examples the bending stiffness ranges from about 1.0 N/mm. to about 5.5 N/mm over a span of 50 mm.

Surface Finish

In some embodiments of the present invention, the distal tubing 121 may comprise different surface finishes to provide various amounts of friction along the exterior surface. In some embodiments, as above the distal tubing 121 may be formed substantially of HDPE. Alternatively, the dilator may be formed from multiple material layers or a composite material. In some such examples, the multiple layers may extend concentrically and longitudinally along the length of the distal tubing 121 in the form of multiple tubular layers. In one such example the inner layer or tubing comprises an HDPE or a low density polyethylene (LDPE) core with an outer layer of PEBAX (polyether block amide) extrusion. This may provide a relatively smoother exterior finish compared to HDPE. Furthermore, the PEBAX tubing allows for silicone coating to be disposed thereon to additionally provide a smooth coating on the exterior.

Alternate Embodiments of the Distal Tip

Figure 3A:
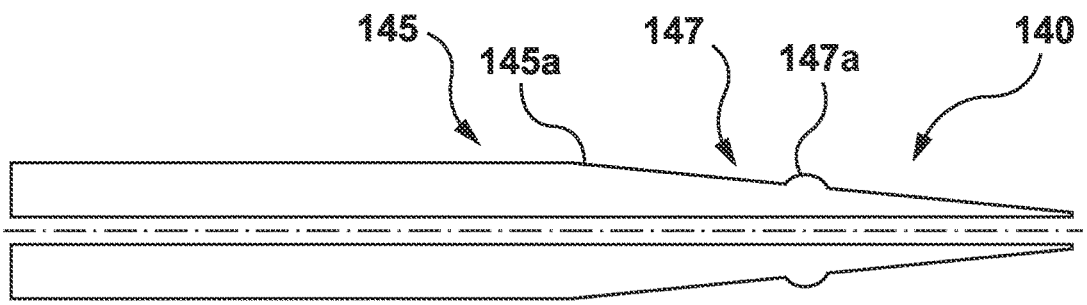
FIGS. 3A-3D illustrate alternate embodiments of a distal tip, in accordance with alternate embodiments of the present invention.
Figure 3B:
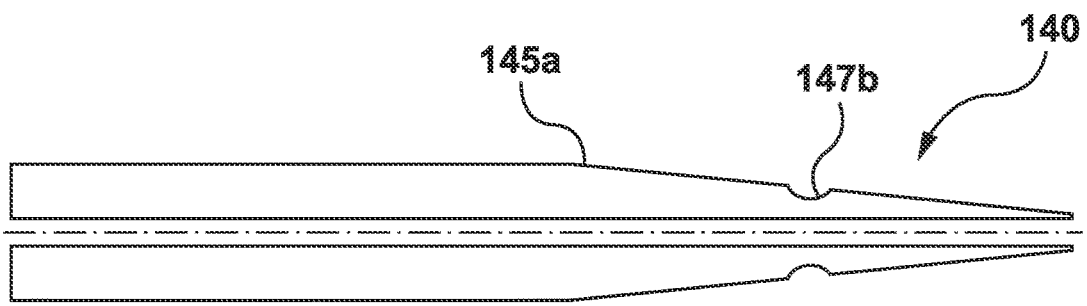

In an alternate embodiment of the present invention, as shown in FIGS. 3A to 3D, the distal tip 140 comprises a modified taper. In one specific example as shown in FIGS. 3A and 3B, the tapered distal tip 140 may comprise a secondary feature such as a secondary surface modification 147 that creates a surface variation, such as a secondary bump 147a or a divot 147b to more closely create the tactile queues of a standard sheath/dilator transseptal kit. The first tactile cue comes from a first/primary feature such as a first surface modification 145, which may be a first bump 145a that is represented by the transition between the tapered tip 140 and the proximal length 123 of the distal tubing 121. As above, the second tactile cue comes from the secondary surface modification 147, for example the secondary bump 147a or divot 147b.

Figure 3C:
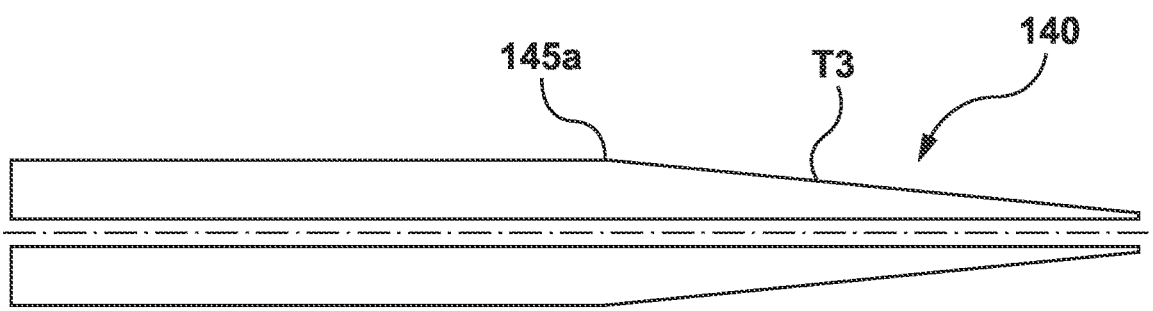
Figure 3D:
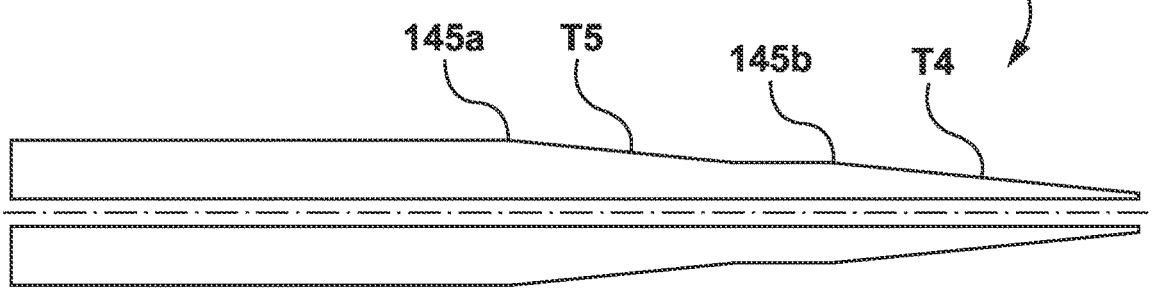

Alternatively, as shown in FIG. 3C, the tapered distal tip 140 may comprise a smooth single external taper T3 with a single surface modification such as a first surface modification 145 in the form of a first bump 145a at the transition, as described previously. In a further alternative, there may be two or more external tapers along the exterior. In a specific example, the distal tip 140 may have two external tapers: external taper T4 and external taper T5 as shown in FIG. 3D, where the first surface modification 145 and secondary surface modification 147 are formed by transitions that form first bump 145a and second bump 145b. These provide tactile cues during use as the hybrid dilator 100 is being advanced through, for example, the septum. The tactile cues mimic the cues that are generally obtained from transitions in a standard transseptal kit that includes a standard dilator and sheath assembly. In some such examples, the internal taper may be as shown in FIG. 2A comprising internal tapers T1 and T2.

Alternatives

In alternative embodiments of the present invention, the distal tip 140 may have a modified external taper T3. In some such examples, the geometry of the external taper T3 may be varied. As outlined previously, the distal tip 140 may have surface modifications along the external taper T3. The external taper T3 may be provided with a secondary bump 147a, the external taper T3 may be provided with divot 147b. Alternatively, the external taper T3 may be provided with a modified roughness.

In alternative embodiments, the ID of the distal tip 140, including internal taper(s), is modified in order to accommodate a crossing/puncturing device such as a needle (for example an RF needle). Alternatively, internal geometry may be modified in order to accommodate a crossing/puncturing device such as a guide wire (for example an RF guidewire). In some embodiments, the shaft distal tubing 121 comprises a single material. Alternatively, the shaft distal tubing 121 may comprise a composite material via co-extrusion or post extrusion processing/layering. In some examples, the shaft distal tubing 121 comprises a lubricious coating material along the exterior. In some such examples, the chemistry and/or processing of the lubricious coating material is varied to provide a suitable coating. In some embodiments, material may be used within the distal tubing 121, and for coating, in accordance with what is known in the art. In a further alternative of the present invention, the hybrid dilator 100 may be provided with forward facing ports along, the distal tip 140, to allow for fluid injection when a needle or a guidewire is positioned inside the hybrid dilator 100.

In some embodiments of the present invention the hybrid dilator 100 has been created to optimize the tubing stiffness/torque response. Also, the handle/hub 112 provides enhanced handing features (discussed further herein below). In some embodiments, as shown previously, the distal tip 140 is provided with two external distal tapers. In some embodiments, the internal controlled geometry may be provided in varying configurations.

Figure 8:
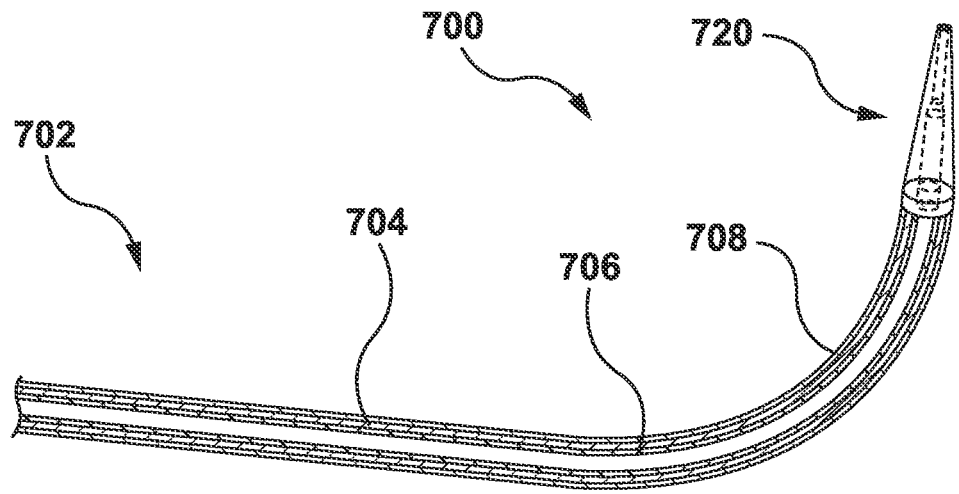
FIG. 8 is a cross sectional view of the shaft and distal tip of a hybrid dilator of an alternative embodiment of the present invention.
Figure 9:
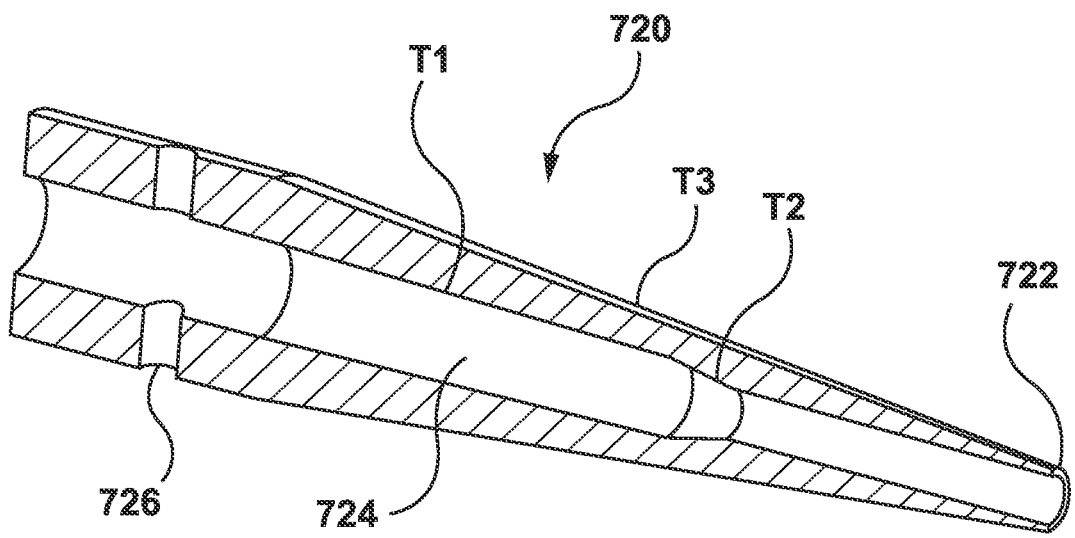
FIG. 9 is an enlarged view of the distal tip of FIG. 8.

FIG. 8 is a cross sectional view of the shaft and distal tip of a hybrid dilator of an alternative embodiment of the present invention and FIG. 9 is an enlarged view of the distal tip of FIG. 8, wherein the dilator shaft has more than one layer and the tip is typically comprised of the same material as one of the shaft layers.

Hybrid dilator 700 of FIG. 8 has a shaft 702 which includes three layers, inner layer 706, outer layer 708, and a middle layer, torque layer 704, to improve the torqueability of the device. There is a smooth joint between device tip 720 and a shaft 702. Inner layer 706 is typically comprised of HDPE and outer layer 708 typically of Pebax or LDPE. Typical embodiments of shaft 702 provide a mechanical response that is similar to transseptal sheath and dilator sets that physicians commonly currently use. The durometer of the Pebax may be selected to adjust the flexibility and pushability of the shaft. The torque layer is typically a braided material, while in alternative embodiments the torque layer may be a stiff polymer and/or a metallic hypotube. Some further embodiments of shaft 702 do not include torque layer 704. While outer layer 708 is typically comprised of Pebax or LDPE, in some alternative embodiments it is made of HDPE, all of which are compatible with lubricious coatings. Typical embodiments of shaft 702 have an outer diameter at least the size of current transseptal sheaths (approximately 0.144" (0.366 cm)) to dilate the septum to at least the same size as current sheaths, and have a mechanical response (including flexibility, pushability, and torqueability) comparable to current transseptal sheath and dilator pairings. Some embodiments of shaft 702 have a 12.5 F outer diameter of about 0.163 inches (0.414 cm) to about 0.166 inches (0.421 cm). Other embodiments of shaft 702 have a 15 F outer diameter of about 0.193 inches (0.490 cm) to about 0.205 inches (0.521 cm). Some embodiments of shaft 702 which have the torque layer 704 have a torque transmission from about 4 N cm to about 8 N cm, with one specific embodiment having a torque transmission of about 8.1 N cm.

In embodiments which include a torque layer 704 between the inner and outer materials (HDPE and Pebax), the braid normally functions as an anchor between the inner and outer layers. Such embodiments may be manufactured using a reflow process which melts both the inner and outer layers into the braided layer whereby the braided layer mechanically joins the two materials together. Some such embodiments have a stainless steel braid and provide 8 N cm of torque transmission.

FIG. 9 illustrates an embodiment of tip 720 typically comprised of HDPE with from about 20 percent to 50 percent of the distal tip being comprised of BaSO4 to facilitate imaging, but alternatively may be comprised of Pebax or any thermoplastic. In some embodiments, tip 720 is comprised of about 40% BaSO4. In testing, HDPE has displayed the advantageous characteristic of being stiff enough to be skive resistant. Tip 720 of FIG. 9 includes internal lumen 724, distal edge 722, and a single external taper T3 for smooth dilation. Internal taper T1 and internal taper T2 guide devices (e.g. guidewires, needles) from the shaft into the tip area, and limits needle protrusion (of compatible needles) out of the end of the dilator. The illustrated example includes two distal side holes 726 for limiting vacuum and pressure formation when withdrawing devices, while alternative examples include different size, location, number of holes, and configuration of holes. Other embodiments of tip 720 include radiopaque features such as bands and coils made from radiopaque materials (e.g. platinum, gold, tungsten, and/or barium sulfate-filled polymer).

Making further reference to FIG. 9, the inner diameter of tip 720 varies from the shaft ID to a smaller diameter compatible with commonly used 0.032" (0.081 cm) or 0.035" (0.089 cm) devices (e.g. guidewires and needles). The length of the external taper T3 is typically more than 1.0 cm long since a shorter length increases the crossing force or may make crossing tissue more abrupt, with some examples of tip 720 having a taper length T3 up to 3 cm in length. In some embodiments, the external taper length of the external taper T3 ranges from about 0.4 inches (1 cm) to about 1 inch (2.5 cm). The outer diameter of tip 720 is typically no greater than 0.055" (0.140 cm) or else the force in advancing through tissue would be larger than typical transseptal dilators. As an example, if the device is 0.032" (0.081 cm) compatible and has an ID of approximately 0.034" (0.086 cm), restraining the tip OD to a maximum of 0.054" (0.137 cm) facilitates smooth advancement through tissue.

In a specific embodiment of the hybrid dilator 700 shown in FIGS. 8 and 9, shaft 702 has an outer diameter of 0.164 inches (0.417 cm) and an inner diameter of 0.072 inches (0.183 cm), the inner diameter of tip 720 at distal edge 722 is compatible with device having outer diameters of 0.032 inches (0.081 cm) or 0.035 inches (0.089 cm), the maximum tip OD is less than 0.055 inches (0.140 cm), the two side holes 726 have diameters of about 0.012 inches (0.030 cm) to about 0.024 inches (0.061 cm), and external taper T3 has a length of 1.6 cm. Typical dilators have a taper length of approximately 1 cm and a smaller diameter than the illustrated embodiment. To prevent hybrid dilator 700 from having a higher taper angle than typical dilators (which results in a higher crossing force), hybrid dilator has an external taper T3 with a length of 1.6 cm which corresponds with its relatively larger outer diameter. In some embodiments, the inner diameter of tip 720 at distal edge 722 is about 0.033 inches (0.084 cm) to about 0.037 inches (0.094 cm) and the outer diameter of tip 720 at distal edge 722 is about 0.040 inches (0.10 cm) to about 0.055 inches (0.14 cm).

Further alternative embodiments of hybrid dilator 700 include outer layer 708 of shaft 702 being made of thermoplastic to facilitate manufacturing. Some examples have only one internal lumen taper or more than two. Some further embodiments include an electrode configured for puncturing at the tip so that the one device can puncture, cross, and dilate.

Some embodiments include the shaft having an inner layer 706 made of HDPE and an outer layer 708 made of Pebax, wherein, during manufacture of the device, tip 720 and inner layer 706 are formed in the same extrusion of HDPE whereby tip 720 and inner layer 706 are continuous without any internal joint, which eliminates the risk of a sharp needle being advanced through the dilator catching at a joint between the dilator shaft 702 and tip 720.

Proximal Hub

Figure 4A:
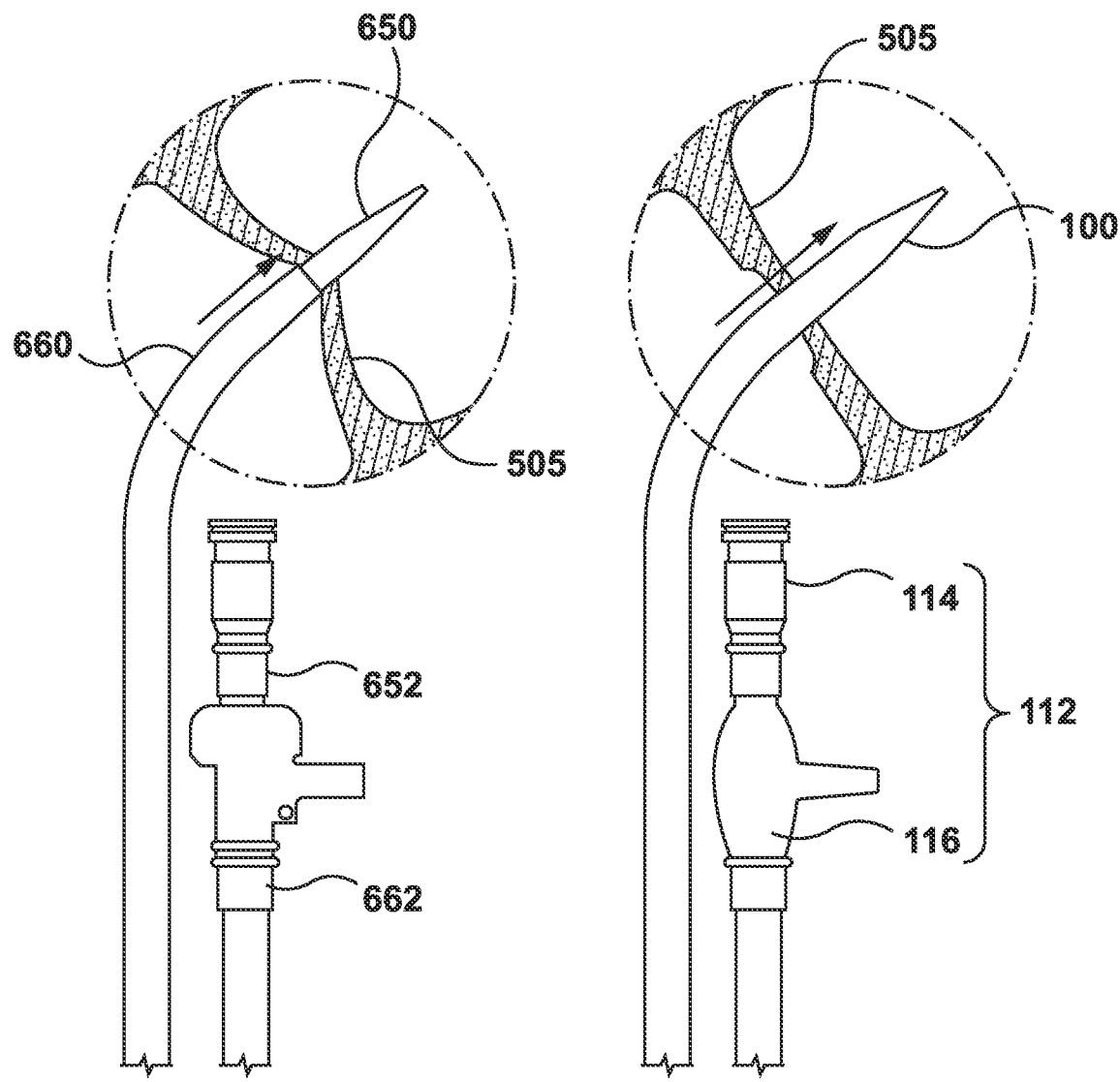
FIG. 4A illustrates a hybrid dilator in accordance with an embodiment of the present invention, and a standard sheath/dilator assembly usable in a standard transseptal procedure.
Figure 4B:
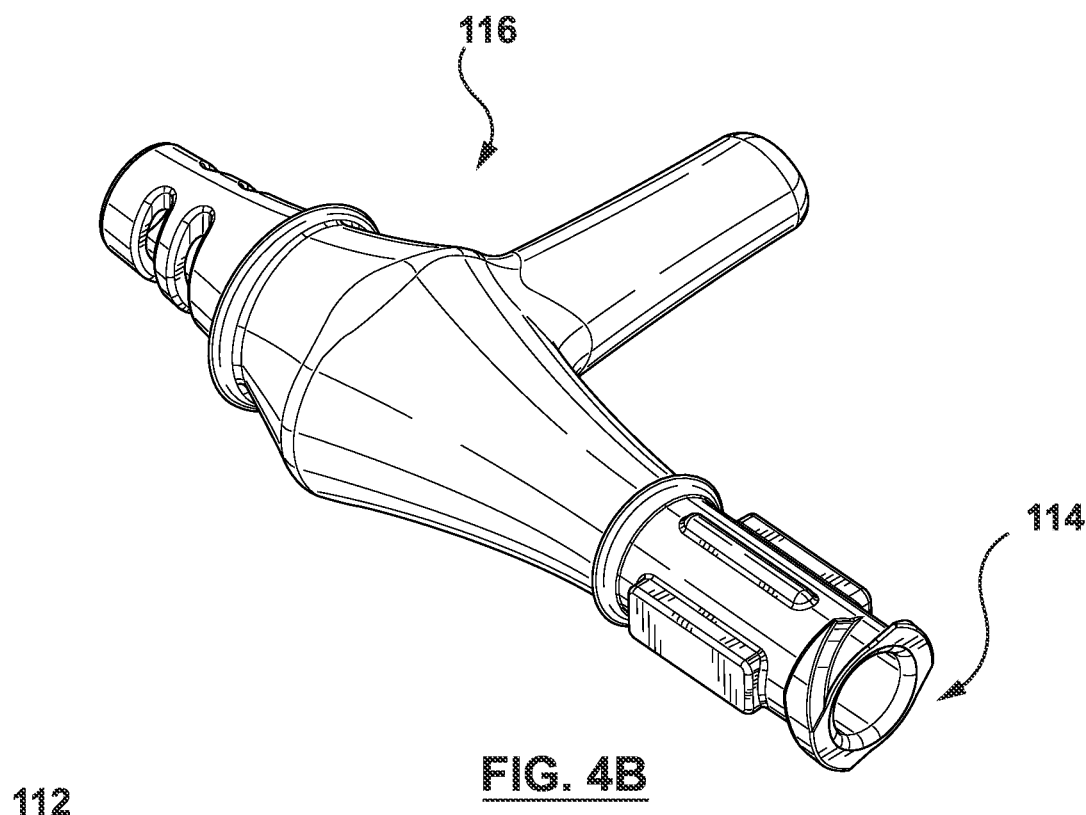
FIGS. 4B-4G illustrate a proximal portion of the hybrid dilator in accordance with an embodiment of the present invention.
Figure 4C:
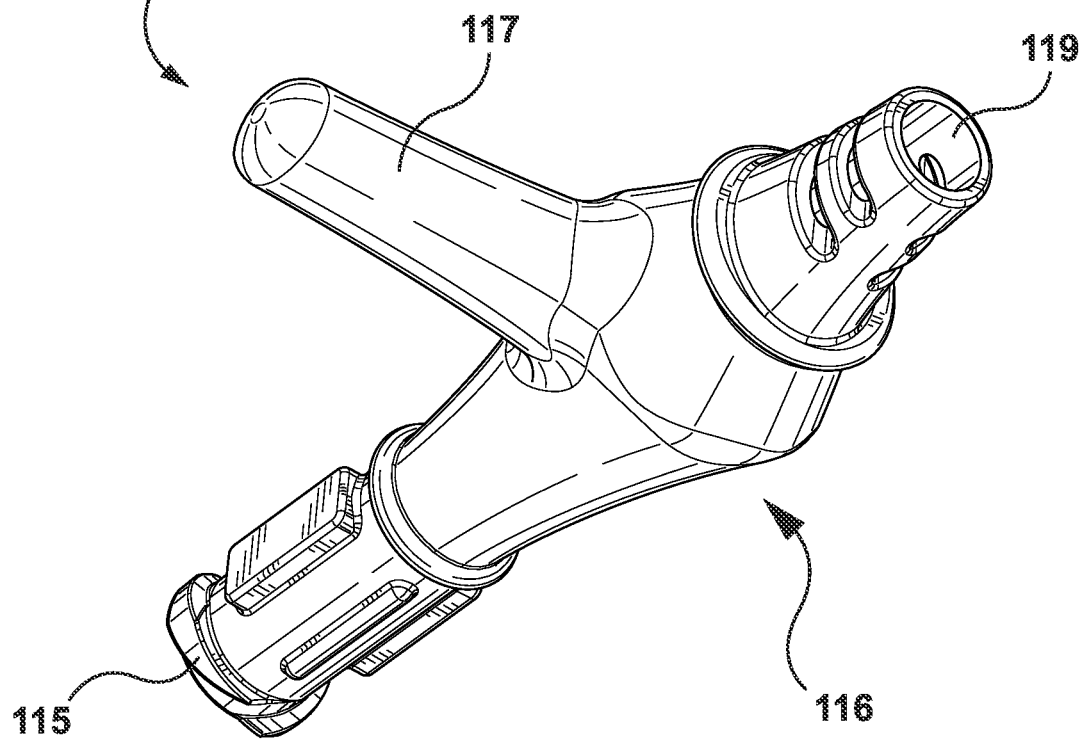
Figure 4D:
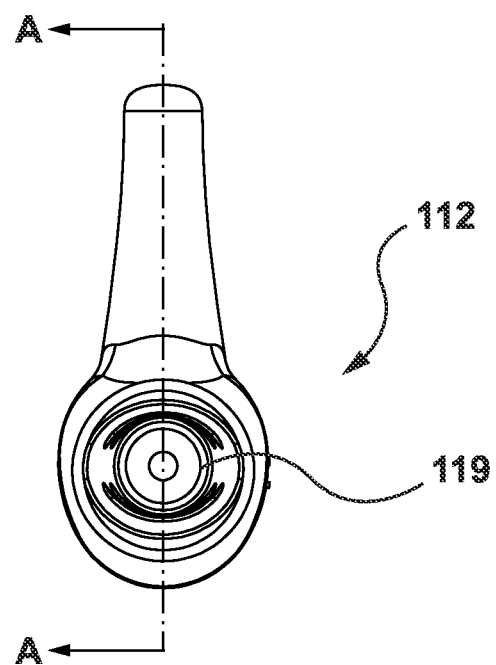
Figure 4E:
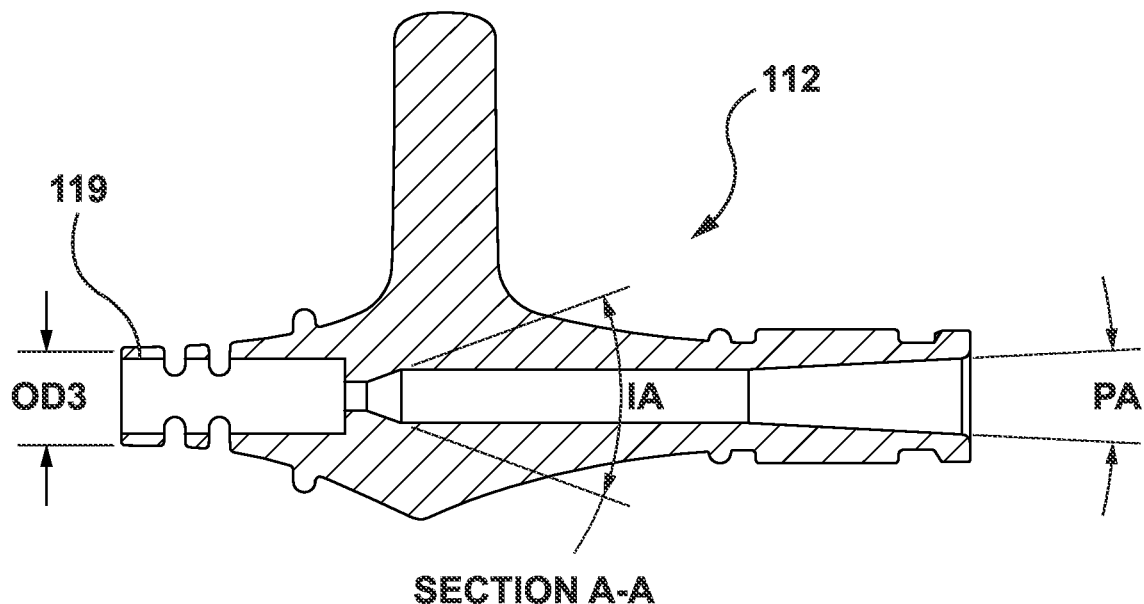
Figure 4F:
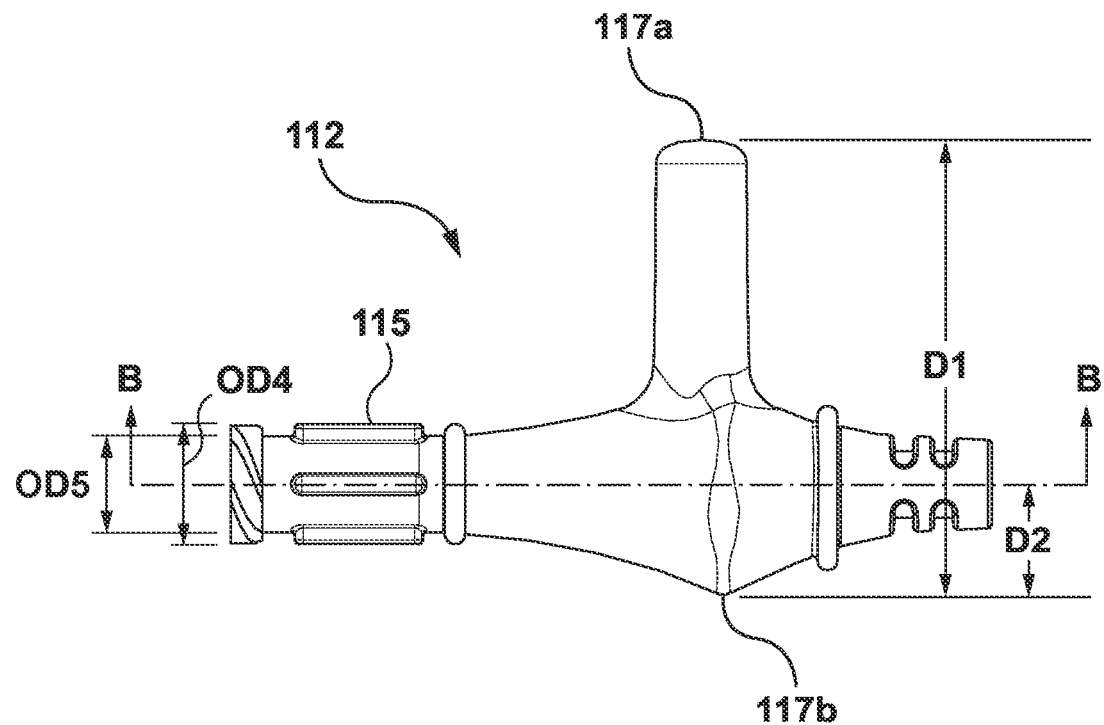
Figure 4G:
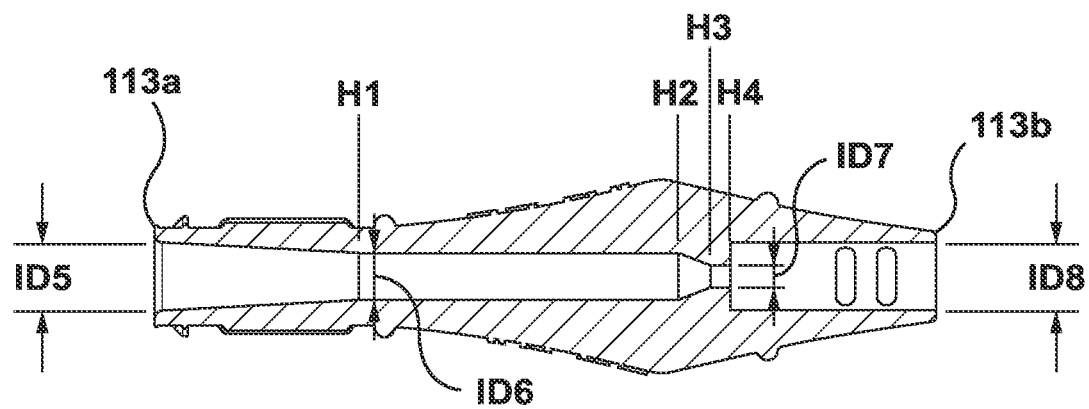

The hybrid dilator 100 comprises a handle defined by a hybrid or combination proximal hub 112 at a proximal end thereof, as additionally shown in FIG. 4A. The proximal hub 112 comprises dilator hub 114 that is formed integrally with a sheath hub or a sheath-like hub 116. FIG. 4A also includes a prior art dilator 650 inserted into sheath 660 such as to show a dilator hub 652 and a sheath hub 662 proximally, and dilator 650 extending out of sheath 660 distally. Sheath 660 and dilator 650 are being advanced across a septum 505 but the heart tissue is catching on sheath 660. In contrast, hybrid dilator 100 which is being advanced across septum 505 without snagging. In some embodiments as shown in FIGS. 4B-4C and 4F, the dilator hub 114 comprises a Lure hub or Luer connector 115 and the sheath hub 116 comprises an arm 117 that functions as pseudo side-port that provides the functional feel of a side-port to provide an indication/direction of the distal end curvature. The arm 117 mimics the side-port of a standard sheath without providing the fluid capability of a standard sheath side-port. The proximal hub 112 forms a hub/handle that is larger than a standard transseptal dilator hub so as to provide the physician with similar handling and expected tactile feedback, by featuring additional material to hold onto and additionally provides the arm 117 to indicate the direction of the distal end curvature. In some examples, the arm 117 may be replaced by functional side-port if the fluid capability is desired. In one specific example, the proximal hub 112 comprises a custom insert molded HDPE Hub at the proximal end with a luer connector 115 and tactile features (defined by a side-port arm 117) to indicate the plane of distal curvature and provide similar handling characteristics. In some such examples, the proximal end 110 has a luer taper to allow for connection of medical syringes or fluid drips. FIG. 4D illustrates an end view taken from a distal end of the proximal hub 112 showing a coupling 119 of the proximal hub 112 for connecting the proximal hub 112 to the distal tubing 121. In some such examples the coupling 119 may comprise a strain relief. FIGS. 4E and 4G show cross-sectional views of the proximal hub 112 illustrating the internal configuration of the proximal hub 112, which may include features for facilitating entry of other devices therein during use. In some such examples, the proximal hub 112 comprises HDPE.

Proximal hub 112, as illustrated in FIG. 4E, includes an outer diameter OD3 of 5.25 mm at its distal end, an internal angle IA of 40.0 degrees, and a proximal angle PA of 6.0 degrees. Proximal hub 112, as illustrated in FIG. 4F, the proximal column has an outer diameter OD5 of 6 mm and an outer diameter of OD4 of 7.37 mm at the Luer connector at its proximal end. The distance D1 between arm endpoint 117a and opposing point 117b is 28.39 mm, and the distance D2 between opposing point 117b and the central longitudinal axis of proximal hub 112 is 6.49 mm. Proximal hub 112, as illustrated in FIG. 4g, has an inner diameter ID5 of 4.25 mm internal to the hub proximal end 113a, an inner diameter ID6 of 3 mm at the innermost portion of the lumen, an inner diameter ID7 at the narrowest portion of the lumen, and an inner diameter ID8 of 4.12 mm at the hub distal end 113b of the hub. Other hub dimensions shown in FIG. 4G include: hub location H1 (at the distal end of the proximal internal taper) is 12.40 mm from hub proximal end 113a, hub location H2 (at the proximal end of the distal internal taper) is 31.83 mm from hub proximal end 113a, hub location H3 (at the distal end of the distal internal taper) is 33.75 mm from hub proximal end 113a, and hub location H4 (at the distal end of narrowest portion of the lumen) is 35 mm from hub proximal end 113a.

Alternate Embodiments of the Proximal Hub

Figure 5A:
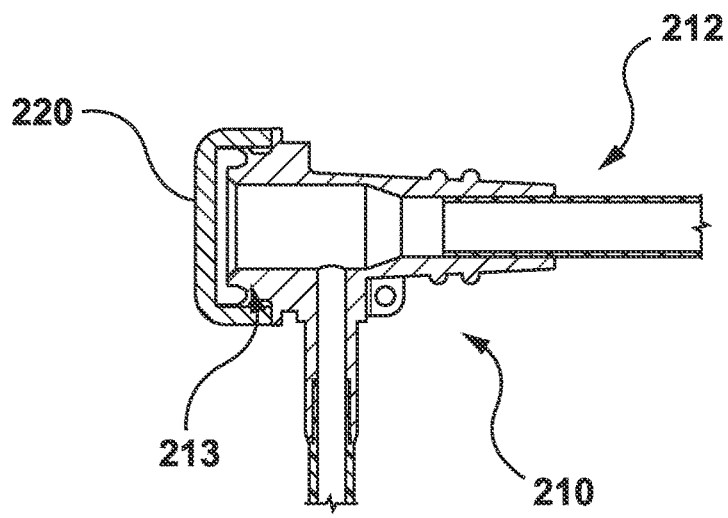
FIGS. 5A-5C illustrates a proximal portion of a hybrid dilator, in accordance with an alternate embodiment of the present invention.
Figure 5B:
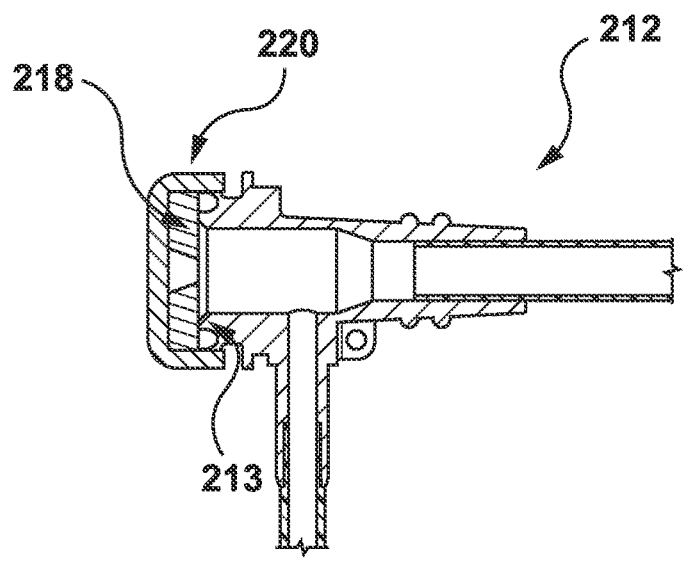
Figure 5C:
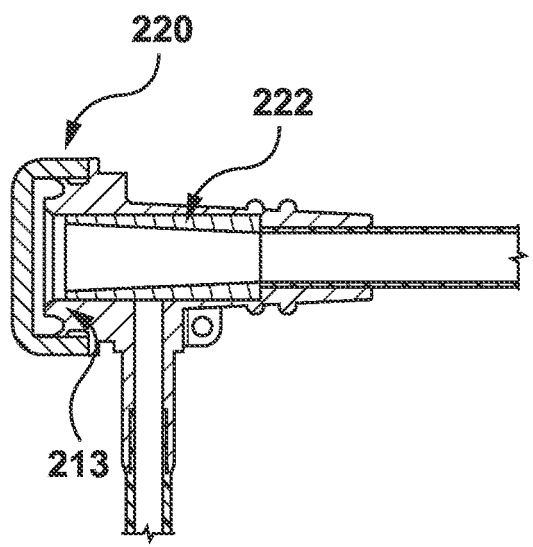

In some embodiments as shown in FIGS. 5A-5D, an alternate embodiment of a hybrid dilator 200 is provided with a modified proximal portion 210. The hybrid dilator 200 comprises a valved proximal hub 212, as shown in FIGS. 5A-5B, where the hub comprises a valve 213 at its proximal end with a cap 220 for retaining the valve in position. The valve 213 is provided as a hemostasis valve. In some examples, as shown in FIG. 5B, the valved proximal hub 212 may additionally comprise an extra feature to direct devices into the valve 213. In some embodiments the proximal hub 212 has an insertion guide 218 as a molded or an external feature that function co-operatively with the valve to direct and align product being inserted into the valve 213. In the particular example shown, the insertion guide 218 is provided proximal of the valve 213.

In accordance with another embodiment of the present invention, a feature is provided within the valved proximal hub 212 to funnel device into the shaft tubing. In a particular case, a funnel guide 222 is provided to direct and align product inserted into valve 213 into the shaft tubing. The funnel guide is positioned distal of the valve 213. In some such examples, the funnel guide 222 is provided as a molded feature. In some embodiments, funnel guide 222 is configured such that it also centers the proximal end of the guidewire with respect to the valve. This centering directs the proximal end of the guidewire when it is inserted through the device's distal tip for the purpose of device exchange.

Figure 5D:
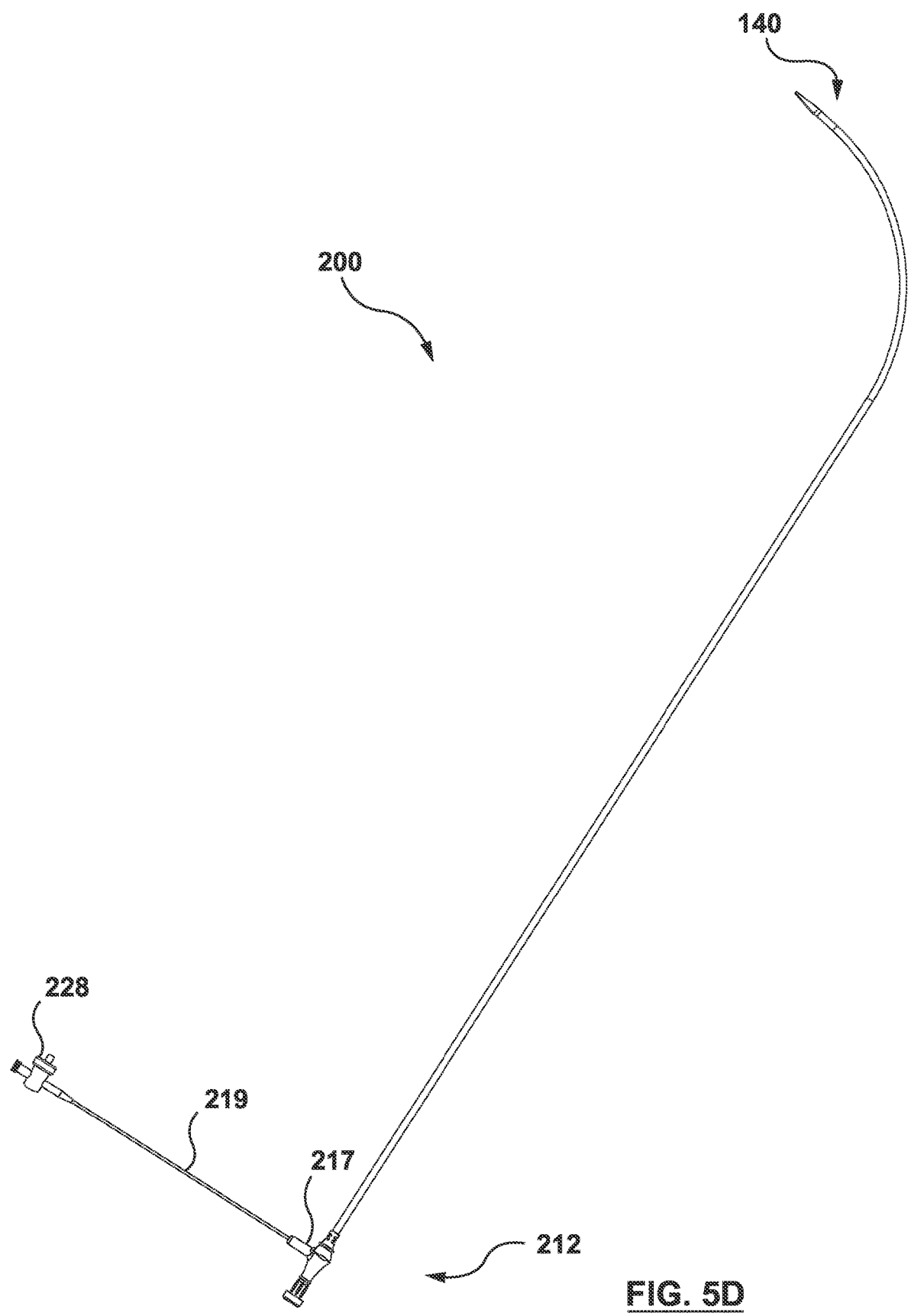
FIG. 5D illustrates a hybrid dilator, in accordance with an alternate embodiment of the present invention.

In a further alternative, as shown in FIG. 5D, a hybrid dilator 200, is provided with a proximal hub 212 that houses a valve 213, for example a hemostasis valve, and additionally comprises a side-port port 217 that has a side-port tubing 219 attached thereto, with a stopcock 228 to provide for flushing and aspiration.

In alternate embodiments of the present invention, the proximal hub 212 may comprise material that is taken from the group consisting of pebax, HDPE, LDPE, and Nylon or a combination thereof to achieve desired lubricity and handling characteristics.

Figure 5E:
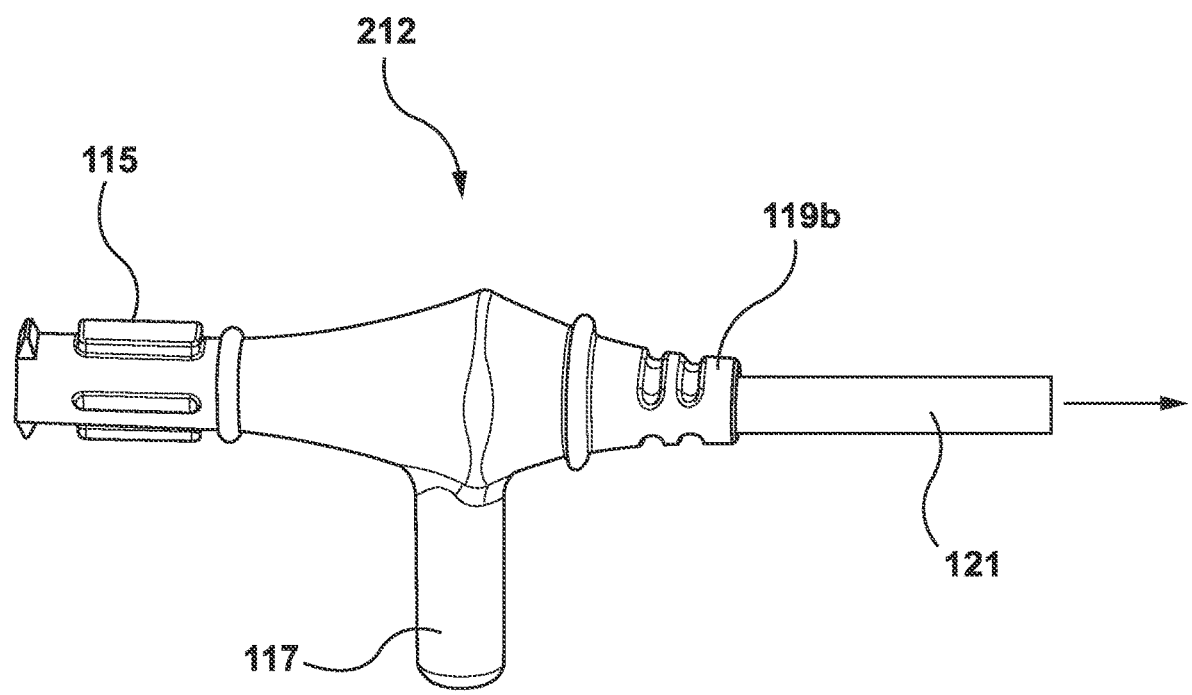
FIG. 5E illustrates an alternative embodiment of a proximal hub, in accordance with an embodiment of the present invention.

In still a further alternative, a proximal hub 112 is shown in FIG. 5E, that comprises a Luer connector 115 according to ISO 594-1,-2. Additionally, an arm 117 is provided in the form of a mock side-port to provide expected handling and align with the distal curve. Additionally, the proximal hub 112 is provided with a strain relief 119b at its distal end and the distal tubing 121 extends in a distal direction out of strain relief 119b.

Alternatives

In some embodiments of the present invention, the proximal hub 112 or valved proximal hub 212 may comprise a molded hub. In some embodiments, the proximal hub 112 or valved proximal hub 212 may comprise HDPE. Alternatively, other materials may be used. In some embodiments, the geometry of the hub may be varied as may be suitable. In alternative embodiments of the valved proximal hub 212, the valve material and/or geometry may be varied as may be known in the art. In some such examples, the slit configuration and/or size may be varied to provide a suitable valve to meet the requirements of the procedure, such as a transseptal procedure. In still further alternatives, the material of the side-port tubing, and the ID and OD of side-port tubing may be selected and/or varied as may be known to a person skilled in the art. Similarly, in some examples, as shown in FIG. 5D where a stopcock is provided, the stopcock material may be varied as may be known in the art.

In still a further alternative of the present invention, some embodiments of a hybrid dilator of the present invention may provide the simplicity of transseptal crossing, and yet may still allow an ablation catheter to be used with it in case the need arises.

Another aspect of the invention is a kit for puncturing a tissue comprising: a crossing device having a puncturing feature; and a hybrid dilator 100, wherein the dilator has a dilator shaft defining a lumen 122 for receiving the crossing device therethrough, the dilator shaft being structured to provide support for the crossing device when the crossing device is used to create a puncture in a tissue. The hybrid dilator also includes a distal tip 140 having an outer diameter which substantially tapers down to an outer diameter of the crossing device for cooperatively providing a smooth profile when the hybrid dilator 100 is advanced through a tissue over the crossing device. In some embodiments of the kit, the crossing device is a mechanical needle with a sharp tip, while in some other embodiments, the crossing device is configured for delivering energy to a tissue.

Another aspect of the invention is a system for puncturing a tissue comprising: a crossing device having a puncturing feature which is operable to deliver energy to a tissue; an electrosurgical generator which is operable to provide energy to the puncturing feature; and a hybrid dilator 100, wherein the hybrid dilator has a dilator shaft defining a lumen 122 for receiving the crossing device therethrough, the dilator shaft being structured to provide support for the crossing device when the crossing device is used to create a puncture in a tissue. The hybrid dilator also includes a distal tip 140 having an outer diameter which substantially tapers down to an outer diameter of the crossing device for cooperatively providing a smooth profile when the hybrid dilator is advanced through a tissue over the crossing device.

Methods of Performing a Transseptal Procedure Using a Hybrid Dilator of the Present Invention In accordance with the present invention, a method of the present invention provides for streamlining the procedural workflow by providing a hybrid dilator that combines the functionalities of a conventional transseptal sheath and dilator assembly. With the hybrid dilator of the present invention a reduced number of devices may be required in order to complete the transseptal procedure, which enhances procedural efficiency while reducing procedural time and complexity.

Figure 6A:
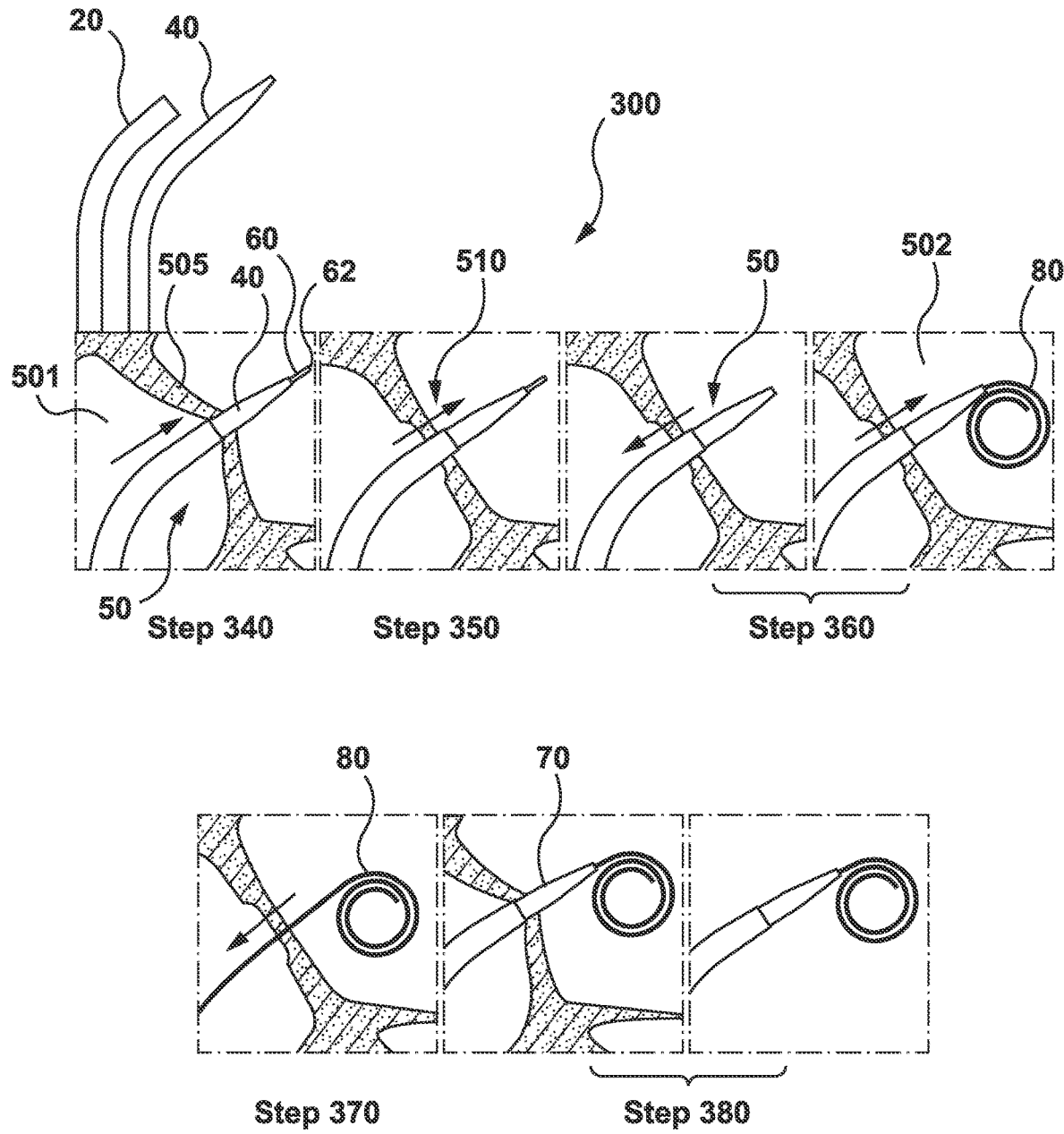
FIG. 6A is an illustration of a method of using a sheath and dilator, in accordance with a standard trans septal procedure.
Figure 6B:
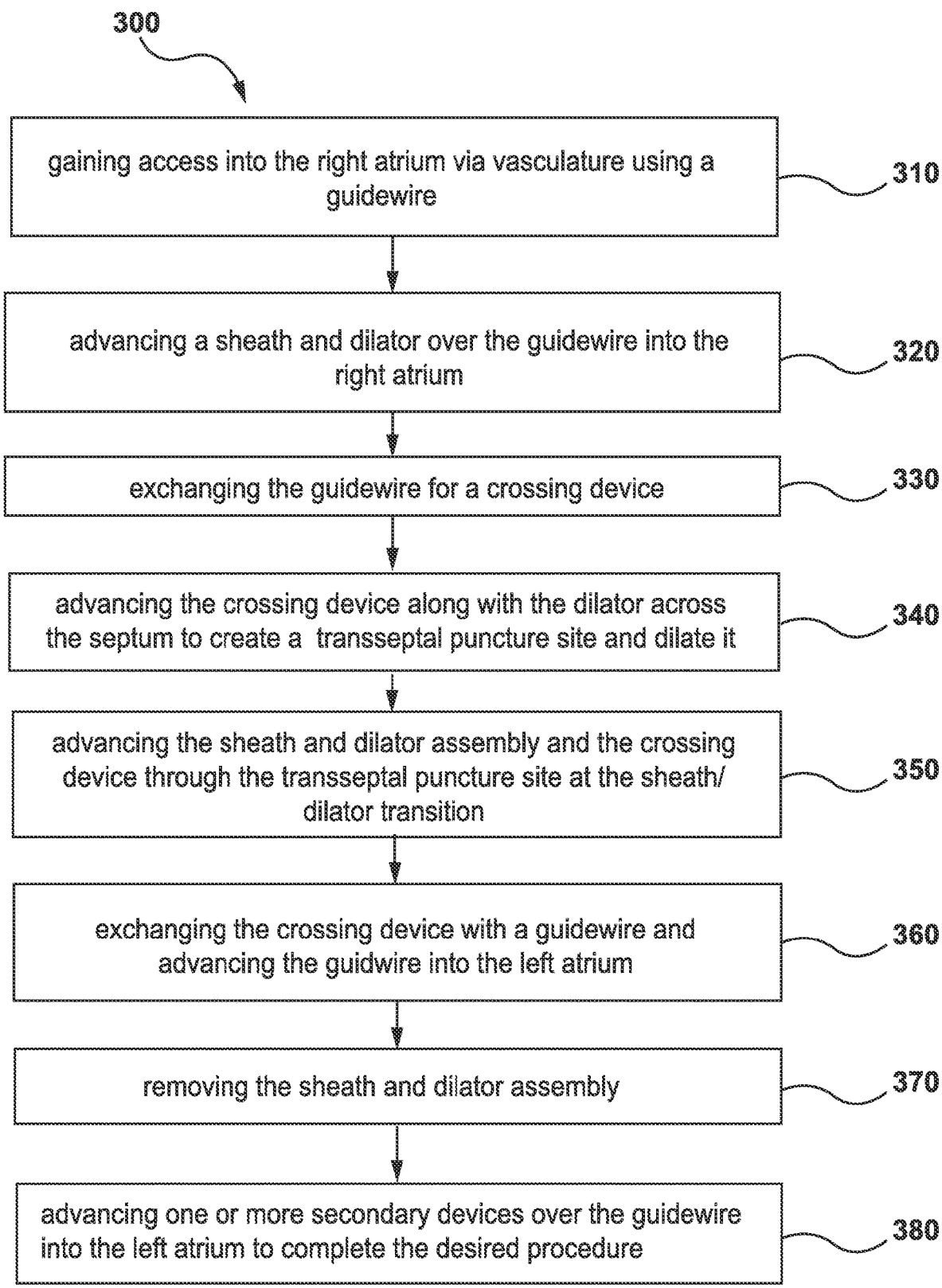
FIG. 6B is a flowchart illustrating steps in a standard transseptal procedure.

In such example, a method of the present invention avoids the disadvantages associated with a conventional transseptal procedure. FIGS. 6A and 6B illustrate an example of method of performing such a conventional transseptal medical procedure 300. The method comprises the steps of: at step 310, gaining access into the right atrium 501 via vasculature using a guidewire; at step 320, advancing a sheath 20 and dilator 40 over the guidewire into the right atrium 501, the sheath 20 and dilator 40 forming a sheath and dilator assembly 50; at step 330, exchanging the guidewire for a crossing device 60 which comprises a puncturing device 62; at step 340, advancing the crossing device 60 along with the dilator across a septum 505 to create a transseptal puncture site 510 and dilate the transseptal puncture site. At step 340, the sheath 20 may get hung up at the sheath/dilator interface and the transition between the sheath/dilator can affect a physician's ability to cross tissue in a predictable, repeatable fashion. Sometimes the physician may not able to cross through to the sheath (get the sheath across the septal puncture site because the tissue will get hung up at the sheath/dilator interface). If at step 350, the physician is successful, the physician may be able to advance the sheath and dilator assembly 50 and the crossing device 60 through the transseptal puncture site 510 to enable the sheath and dilator transition to cross the puncture site 510. In some such procedures, the physician may wish to use a relatively large delivery sheath (for example which is larger than the transseptal sheath 20) for complex procedures for example for cryoablation procedures or a left atrial appendage closure/occlusion procedure and knows they cannot cross with the large delivery sheath, so the physician will introduce a standard transseptal kit with the sheath and dilator as discussed at step 350 above to purely to cross and pre-dilate the septum. Once this three piece kit is removed for exchange, it must be disposed, thereby underutilizing the three items (sheath, dilator, guidewire) for only a short procedural presence. The removal of the sheath/dilator assembly and exchange with the larger delivery sheath is described further below. At step 360 of the method, the crossing device 60 is exchanged with a guidewire 80, which comprises the steps of removing the crossing device 60 and advancing the guidewire 80 into the left atrium 502; at step 370, removing the sheath and dilator assembly 50; and at step 380, advancing one or more secondary devices 70 such as a relatively large delivery sheath over the guidewire 80 into the left atrium 502 to complete the desired procedure.

Figure 7A:
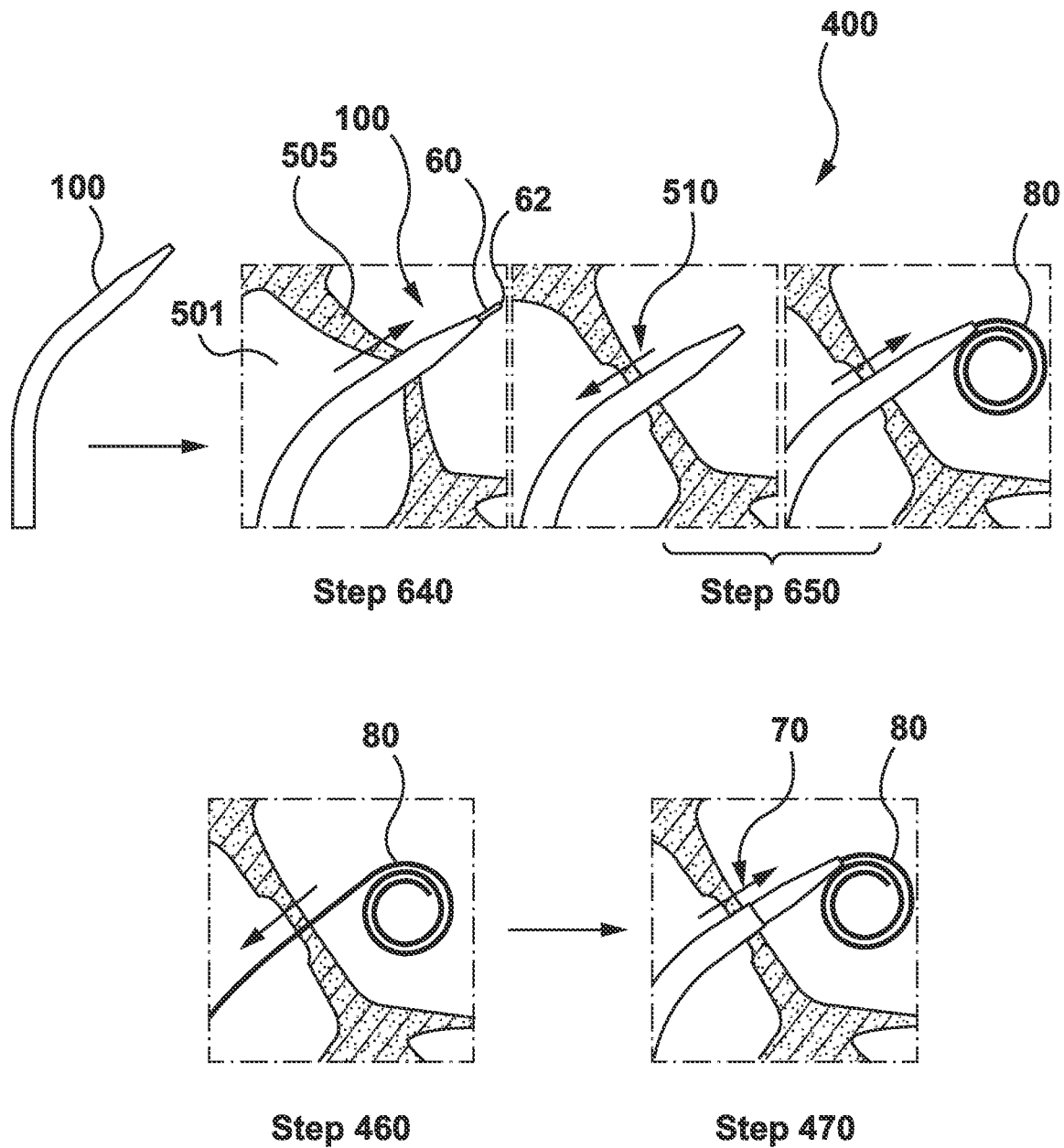
FIG. 7A is an illustration of a method for performing a transseptal puncture procedure using a hybrid dilator, in accordance with an embodiment of the present invention.
Figure 7B:
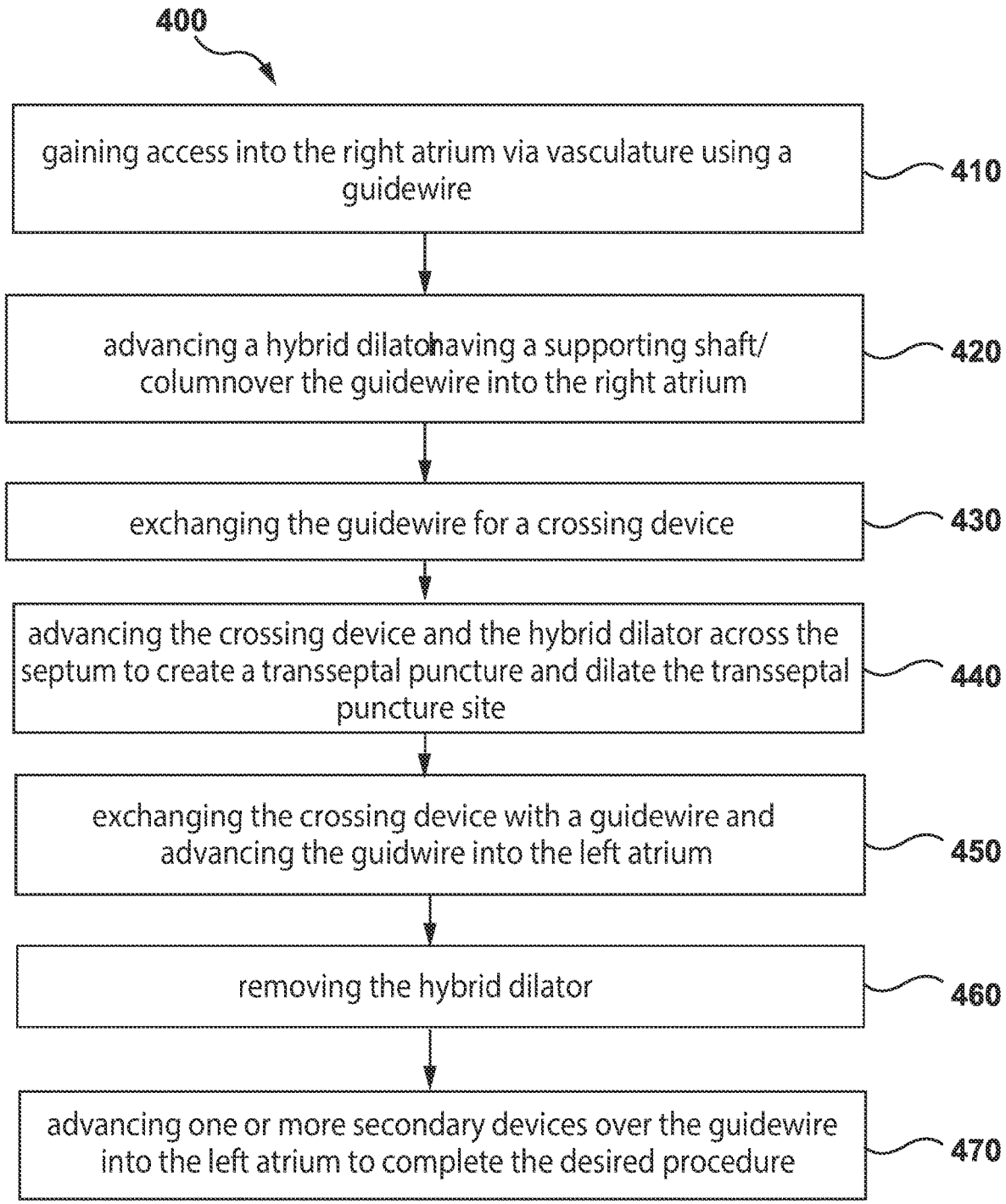
FIG. 7B is a flowchart illustrating steps of a method for performing a transseptal puncture procedure using a hybrid dilator, in accordance with an embodiment of the present invention

As outlined herein above, embodiments of the present invention provide an optimized transseptal procedure In accordance with a method of the present invention, as shown in FIGS. 7A and 7B, an optimized method 400 is provided for carrying out a transseptal procedure. The method comprises the steps of: at step 410, gaining access into the right atrium via vasculature using a guidewire; and at step 420, advancing a hybrid dilator 100 having a supporting shaft/column over the guidewire into the right atrium 501; By using the hybrid dilator 100 it reduces number of parts that the physician is required to prep/assemble and introduce into the patient from three to two.

Instead of a sheath, dilator and guidewire, a hybrid dilator 100 and guidewire may be used. The method additionally provides: at step 430, exchanging the guidewire for a crossing device 60 which comprises a puncturing device 62 [In some embodiments of the present invention, the puncturing device 62 may comprise a needle. In some such examples, the needle is a radiofrequency (RF) needle. Alternatively, the needle may comprise a mechanical needle. In other embodiments of the present invention, the puncturing device 62 may comprise a radiofrequency (RF) guidewire]; and at step 440 advancing the crossing device and the hybrid dilator across the septum 505 to create a trans septal puncture site 510 and dilate the puncture site 510 to facilitate advancement of one or more secondary devices 70 through the transseptal puncture site. The hybrid dilator 100, which may also be referred to as the step-up dilator, is provided as a simplified tool. It simplifies the procedural workflow by providing a one piece transseptal tool compared to a sheath and dilator (it is additionally usable with a guidewire and needle as shown). The hybrid dilator 100 is provided as a one/single oversized dilator and in use it reduces the number of physical/geometric transitions as well as the number of material transitions or tactile obstructions which may allow the physicians to complete a transseptal or other tissue crossings with greater ease. The hybrid dilator 100 reduces the changes of the hybrid dilator 100 from getting caught at the transseptal puncture site, by provided smooth lines and tapers to facilitate a seamless transition across tissue. This allows the hybrid dilator 100 to be advanced across the septum with greater ease. The method additionally provides for; at step 450, exchanging the crossing device 60 with a guidewire 80 and advancing the guidewire 80 into the left atrium; at step 360, removing the hybrid dilator 100; and at step 470, advancing the one or more secondary devices over the guidewire 80 into the left atrium 502 to complete the desired procedure.

In procedures where the physician wishes to use a relatively large delivery sheath for complex procedures (for example for cryoablation or LAA occlusion) and knows they cannot cross with that product, the physician can now introduce just the hybrid dilator 100 over a guidewire as discussed in step 420 using a single device to cross and pre-dilate the septum. The hybrid dilator 100 and the initial guidewire may then be removed for exchange, thus using only two products (hybrid dilator 100 and guidewire, instead of a standard sheath, dilator and guidewire kit). As such the improved method additionally provides at steps 460 and 470 removing just the hybrid dilator 100 to allow exchange with the secondary device such as a relatively large delivery sheath for complex procedures, wasting fewer products in the process.

Another embodiment of the method of uses a hybrid dilator 100 and a crossing device for puncturing a septum 505 of a heart. This embodiment of the method comprises the steps of: a) positioning a distal tip 140 of the hybrid dilator at a desired site of the septum; b) using the hybrid dilator 100 for supporting a crossing device, located within a lumen of the hybrid dilator, as the crossing device is advanced beyond the distal tip of the hybrid dilator to puncture the septum; and c) advancing the hybrid dilator over the crossing device thereby dilating the desired site. In some such embodiments, the crossing device is a mechanical needle and step (b) further includes applying force with the mechanical needle to the septum to thereby puncture the septum. In other embodiments, the crossing device is configured for delivering energy, and step (b) further includes supplying electrical energy to the crossing device to thereby puncture the septum. Some embodiments further comprise a step (d) of exchanging the crossing device with a guidewire and advancing the guidewire into a left atrium, a step (e) of removing the hybrid dilator, and a step (f) of advancing one or more secondary devices over the guidewire into the left atrium.

In some embodiments of using a hybrid dilator and a crossing device for puncturing a septum of a heart wherein the crossing device is configured for delivering energy, the crossing device is further configured for use as a guide-wire, and the method further comprises a step (d) of removing the hybrid dilator, and, typically, a step (e) of advancing one or more secondary devices over the crossing device into a left atrium. Further details of crossing devices suitable for delivering energy and using as a guide-wire are given in international application PCT/IB2013/060287, entitled "METHODS AND DEVICES FOR PUNCTURING TISSUE", which is hereby incorporated-by-reference in its entirety.

As such, in accordance with embodiments of the present invention, a method is provided for streamlining the procedural workflow by providing a hybrid dilator that combines the functionalities of a conventional transseptal sheath and dilator assembly. With the hybrid dilator of the present invention a reduced number of devices may be required in order to complete the transseptal procedure, which enhances procedural efficiency while reducing procedural time and complexity.

The problem of a transseptal puncture being performed using a crossing device which is supported by a sheath and dilator set having a transition which may snag on tissue when crossing the septum, can be addressed by using a hybrid dilator (described herein) instead of the sheath and dilator set to thereby eliminate the transition, wherein the hybrid dilator has the appropriate functionality (flexibility, pushability, torqueability, distal taper, etc.) to facilitate a smooth crossing.

The embodiment(s) of the invention described above are intended to be exemplary only. The scope of the invention is therefore intended to be limited solely by the scope of the appended claims.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the broad scope of the appended claims. All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

The invention claimed is:

1. A hybrid dilator for use with a crossing device in tissue puncturing procedures, the hybrid dilator comprising:
   a dilator shaft extending between a proximal end and a distal end, the dilator shaft having a lumen for receiving a crossing device therethrough;
   a distal tip associated with the distal end, the distal tip having an external taper region defined by an outer diameter which tapers to an outer diameter of the crossing device for providing a smooth transition between the crossing device and the distal tip when the crossing device is inserted through the lumen and protrudes beyond the distal tip and internal taper region defined by an inner diameter wherein the lumen includes a plurality of tapers separated by a longitudinal portion, the internal taper region positioned within the external taper region; and
   a hub coupled to the dilator shaft defining a lumen therethrough, wherein the hub has a side arm configured to manipulate the hub as a user handle.

2. The hybrid dilator of claim 1, wherein the dilator shaft further comprises a distal end curvature.

3. The hybrid dilator of claim 2, wherein the side arm provides an indication of the direction of the distal end curvature.

4. The hybrid dilator of claim 1, wherein the side arm is a pseudo side-port.

5. The hybrid dilator of claim 1, wherein the side arm is a side-port.

6. The hybrid dilator of claim 1, wherein the dilator shaft is structured to provide support for the crossing device when the crossing device is used to create a puncture in a tissue.

7. The hybrid dilator of claim 1, wherein the hybrid dilator further comprises a coupling for providing strain relief between the hub and dilator shaft.

8. The hybrid dilator of claim 1, wherein the side arm has an endpoint and the distance between the side arm endpoint and an opposing point on the hub is 28.39 mm.

9. The hybrid dilator of claim 1, wherein the dilator shaft has an outer diameter from about 12 French to about 20 French.

10. The hybrid dilator of claim 1, wherein a distal portion of the distal tip defines a distal internal diameter which is restricted to thereby control a distance by which a crossing device with a narrow distal portion protrudes from the hybrid dilator.

11. The hybrid dilator of claim 1, wherein the dilator shaft comprises an inner layer, an outer layer, and a torque layer therebetween.

12. The hybrid dilator of claim 11, wherein the torque layer is comprised of a braided material.

13. The hybrid dilator of claim 1, wherein the distal tip comprises a divot configured to provide a tactile queue.

14. The hybrid dilator of claim 1, wherein the distal tip is comprised of high density polyethylene, and wherein from about 20 percent to 50 percent of the distal tip is comprised of $BaSO_4$ to facilitate imaging.

15. A kit for puncturing a tissue comprising:
   a crossing device having a puncturing feature; and
   a hybrid dilator having:
      a dilator shaft extending between a proximal end and a distal end, the dilator shaft having a lumen for receiving a crossing device therethrough;
      a distal tip associated with the distal end, the distal tip having an external taper region defined by an outer diameter which tapers to an outer diameter of the crossing device for providing a smooth transition between the crossing device and the distal tip when the crossing device is inserted through the lumen and protrudes beyond the distal tip and internal taper region defined by an inner diameter wherein the lumen includes a plurality of tapers separated by a longitudinal portion, the internal taper region positioned within the external taper region; and
      a hub coupled to the dilator shaft defining a lumen therethrough, wherein the hub has a side arm configured to manipulate the hub as a user handle.

16. The kit of claim 15, wherein the crossing device is a mechanical needle.

17. The kit of claim 15, wherein the crossing device comprises an energy delivery device that is configured for delivering energy to the tissue to create a puncture in the tissue.

18. The kit of claim 17, wherein the energy delivery device comprises a radiofrequency needle.

19. The kit of claim 17, wherein the energy delivery device comprises a radiofrequency guidewire.

20. A system for puncturing a tissue comprising:
- a crossing device having a puncturing feature which is operable to deliver energy to a tissue;
- an electrosurgical generator which is operable to provide energy to the puncturing feature; and
- a hybrid dilator having:
  - a dilator shaft extending between a proximal end and a distal end, the dilator shaft having a lumen for receiving a crossing device therethrough;
  - a distal tip associated with the distal end, the distal tip having external taper region defined by an outer diameter which tapers to an outer diameter of the crossing device for providing a smooth transition between the crossing device and the distal tip when the crossing device is inserted through the lumen and protrudes beyond the distal tip and an internal taper region defined by an inner diameter wherein the lumen includes a plurality of tapers separated by a longitudinal portion, the internal taper region positioned within the external taper region; and
  - a hub coupled to the dilator shaft defining a lumen therethrough, wherein the hub has a side arm configured to manipulate the hub as a user handle.

* * * * *